United States Patent [19]

Huang et al.

[11] Patent Number: 4,584,303

[45] Date of Patent: Apr. 22, 1986

[54] N-ARYL-N-(4-PIPERIDINYL)AMIDES AND PHARMACEUTICAL COMPOSITIONS AND METHOD EMPLOYING SUCH COMPOUNDS

[75] Inventors: Bao-Shan Huang, Edison; Ross C. Terrell, Clark; Kirsten H. Deutsche, Morristown; Linas V. Kudzma, North Bergen, all of N.J.; Nhora L. Lalinde, West Nyack, N.Y.

[73] Assignee: The BOC Group, Inc., Montvale, N.J.

[21] Appl. No.: 707,433

[22] Filed: Apr. 17, 1985

Related U.S. Application Data

[63] Continuation-in-part of Ser. No. 598,769, Apr. 9, 1984, abandoned.

[51] Int. Cl.$^4$ .................. A61K 31/445; C07D 405/12; C07D 417/12; C07D 401/12
[52] U.S. Cl. ..................................... 514/326; 514/329; 546/207; 546/209; 546/210; 546/212; 546/213; 546/221; 546/222; 546/224
[58] Field of Search ............... 546/207, 209, 210, 212, 546/213, 222, 221, 224; 514/326, 329

[56] References Cited

U.S. PATENT DOCUMENTS

| | | | |
|---|---|---|---|
| 3,161,637 | 12/1964 | Janssen | 546/213 |
| 3,164,600 | 1/1965 | Janssen | 546/213 |
| 3,998,834 | 12/1976 | Janssen et al. | 546/224 |
| 4,196,210 | 4/1980 | Sanczuk et al. | 546/213 |

*Primary Examiner*—Robert T. Bond
*Attorney, Agent, or Firm*—Arnold H. Krumholz; Roger M. Rathbun; Larry R. Cassett

[57] ABSTRACT

Compounds are disclosed of the formula

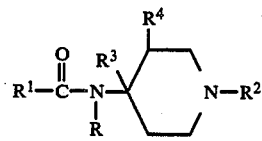

optically active isomeric forms thereof, and/or pharmaceutically acceptable acid addition salts thereof, in which formula: R is defined in the disclosure.

132 Claims, No Drawings

N-ARYL-N-(4-PIPERIDINYL)AMIDES AND PHARMACEUTICAL COMPOSITIONS AND METHOD EMPLOYING SUCH COMPOUNDS

This application is a continuation-in-part of U.S. application Ser. No. 598,769 filed Apr. 9, 1984, now abandoned.

The present invention relates to N-aryl-N-(4-piperidinyl) substituted alkoxyalkylamides, furoylamides or thiophene carboxamides and methods and compositions employing such compounds.

A number of patents disclose certain N-phenyl-N-(4-piperidinyl)amides having analgesic activity. For example, some such compounds are disclosed in U.S. Pat. Nos. 3,164,600 and 3,998,834. U.S. Pat. No. 4,196,210 discloses N-aryl-N-(1-substituted-4-piperidinyl) aryl acetamides useful as anti-arrhythmic agents. U.S. Pat. No. 4,197,236 discloses other similar piperidinyl compounds as being stabilizers for organic materials.

SUMMARY OF THE INVENTION

It has now been found that very desirable analgesic properties are provided by compounds of the formula:

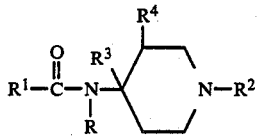
(I)

optically active isomeric forms thereof, and/or pharmaceutically acceptable acid addition salts thereof. In the Formula (I) above, R is selected from the group consisting of phenyl and substituted phenyl wherein the substituents are selected from halogen, cyano, lower-alkoxy, lower-alkyl, lower-alkylenedioxy, halogenated, lower-alkyl, lower-alkylthio, or combinations thereof. $R^1$ is selected from a furanyl group, a thienyl group or a group of the formula

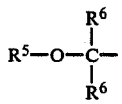

wherein $R^5$ is selected from lower-alkyl, lower-cycloalkyl, halogenated lower-alkyl, phenyl, or phenyl-lower-alkyl and wherein each $R^6$ is independently selected from hydrogen, lower-cycloalkyl or lower-alkyl. $R^2$ is selected from the group consisting of phenylalkyl; lower-alkyl; lower-alkenyl; lower-alkynyl; halogenated lower-alkyl; (cycloalkyl)alkyl; thienyl lower-alkyl; thiazolyl lower-alkyl which can be substituted in the 4-position with a methyl group; (4,5-dihydro-5-oxo-1H-tetrazol-1-yl) lower-alkyl which can be substituted in the 4-position with a group selected from lower-alkyl, lower-cycloalkyl, aryl or aryl lower-alkyl; and substituted phenyl lower-alkyl in which the substituents on the phenyl ring are selected from halogen, cyano, lower-alkoxy, lower-alkyl, lower-alkylenedioxy, halogenated lower-alkyl, lower-alkylthio or combinations thereof. $R^3$ is selected from a group consisting of hydrogen, methoxymethyl, and a carboxylate radical represented by the formula

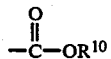

wherein $R^{10}$ is selected from the group consisting of lower-alkyl, aryl-lower-alkyl, lower-alkoxy-lower-alkyl and aryloxy lower-alkyl. $R^4$ is selected from hydrogen or methyl.

One class of compounds within this scope are compounds of the formula:

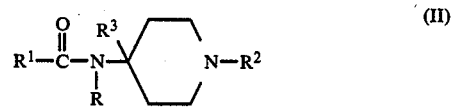
(II)

optically active isomeric forms thereof, and/or pharmaceutically acceptable acid addition salts thereof. In the Formula (II) above, R is selected from the group consisting of phenyl and substituted phenyl wherein the substituents are selected from halogen, lower-alkoxy, lower-alkyl, or combinations thereof. $R^1$ is a furanyl group or a group of the formula

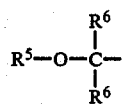

wherein $R^5$ is lower-alkyl or lower-cycloalkyl, and wherein each $R^6$ is independently selected from hydrogen, lower-alkyl or lower-cycloalkyl. $R^2$ is a group of the formula

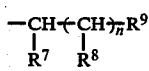

wherein each $R^7$ and $R^8$ are each independently selected from hydrogen, phenyl, or lower-alkyl. $R^9$ is selected from the group consisting of phenyl; thienyl; 4,5-dihydro-5-oxo-1H-tetrazol-1-yl; 4,5-dihydro-5-oxo-1H-tetrazol-1-yl substituted in the 4-position by a group selected from lower-alkyl, aryl-lower-alkyl or aryl; and substituted phenyl wherein the substituents are selected from halogen, lower-alkoxy, lower-alkyl, or combinations thereof. n is an integer of from 0 to 7. $R^3$ is selected from a group consisting of hydrogen, methoxymethyl, and a carboxylate radical represented by the formula

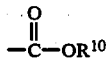

wherein $R^{10}$ is selected lower-alkyl, aryl-lower-alkyl or lower-alkoxy-lower-alkyl.

The compounds of the invention have central nervous system depressant properties which include analgesia, hypnosis, sedation, muscle relaxation, increased pain threshold, and barbiturate and/or general anesthesic potentiation. Many of the compounds provide highly potent analgesia with a short duration of action. This is highly desirable in circumstances where acute severe pain has to be eliminated over a short period of time, e.g., anesthesiology. Certain of these compounds have also been found to provide reduced rigidity at high doses, or equal or less respiratory and cardiac depression when compared to fentanyl. The compounds of the invention can be used together with a pharmaceutically acceptable carrier to provide pharmaceutical compositions and can be administered to mammals such as man in amounts sufficient to provide analgesic effects.

One preferred class of compounds is the same as that broadly described above but wherein $R^1$ is furanyl, thienyl, methoxymethyl or 1-methoxyethyl.

With regard to other substituents in the compounds of the invention, the compounds wherein R is a phenyl ring substituted in the 2-position represent another preferred class. Examples of such 2-substituents include halogen (preferably chloro or fluoro), lower-alkoxy (preferably methoxy), or lower-alkyl (preferably methyl or ethyl).

One preferred class of compounds within the scope of the present invention are of the formula

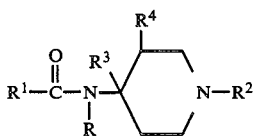

optically active isomeric forms thereof, and/or pharmaceutically acceptable acid addition salts thereof, in which formula: R is phenyl or 2-substituted phenyl wherein said 2-substituent is selected from halogen (preferably chloro or fluoro), lower-alkoxy (preferably methoxy), or lower-alkyl (preferably methyl or ethyl); $R^1$ is methoxymethyl, 1-methoxyethyl, thienyl, or furanyl; $R^2$ is selected from the group consisting of 2-phenylethyl, 2-(2-fluorophenyl)ethyl, 1-phenyl-2-propyl, 2-phenyl-1-propyl, 2-(3-thienyl)ethyl, 2-(2-thienyl)ethyl, 2-(4-methylthiazol-5-yl)ethyl, 2-(4-ethyl-4,5-dihydro-5-oxo-1H-tetrazol-1-yl)ethyl and 2-methyl-1-propyl; $R^3$ is selected from the group consisting of hydrogen, methoxymethyl and a methyl carboxylate group; and $R^4$ is selected from hydrogen or methyl.

Another preferred class of compounds within the scope of the invention are of the formula

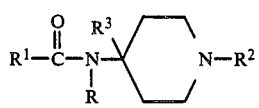

optically active isomeric forms thereof, and/or pharmaceutically acceptable acid addition salts thereof, in which formula: R is phenyl; $R^1$ is methoxymethyl or furanyl; $R^2$ is selected from the group consisting of 2-phenylethyl, 1-phenyl-2-propyl, 2-phenyl-1-propyl, and 2-(2-thienyl)ethyl; and $R^3$ is hydrogen, methoxymethyl or a methyl carboxylate group.

DETAILED DESCRIPTION OF THE INVENTION

As noted above, the compounds of the invention have the formula

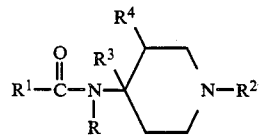 (I)

wherein R, $R^1$, $R^2$, $R^3$, and $R^4$ are as defined above. The compounds can be in the form of pharmaceutically acceptable acid addition salts, optically active isomers, and/or cis/trans isomers thereof.

The group R in Formula I above can be selected from the group consisting of phenyl and substituted phenyl wherein the substituents are selected from halogen, cyano, lower-alkoxy, lower-alkyl, lower-alkylenedioxy, halogenated lower-alkyl, lower-alkylthio or combinations thereof. A preferred substituted phenyl includes a substituent in the 2-position thereof such as halogen (preferably F or Cl), lower-alkyl (preferably $CH_3$ or $CH_3CH_2$), lower-alkoxy (preferably $CH_3O-$), halogenated lower-alkyl (preferably trifluoromethyl), lower-alkylthio (preferably methylthio), or cyano. Suitable R substituents include phenyl, 2-ethylphenyl, 2,6-dimethylphenyl, 2-methylthiophenyl, 2-trifluoromethylphenyl, 2-chlorophenyl, 3-chlorophenyl, 4-chlorophenyl, 2-methoxyphenyl, 3-methoxyphenyl, 2-fluorophenyl, 3-fluorophenyl, 4-fluorophenyl, 2-methoxy-3-chlorophenyl, 3-chloro-4-methoxyphenyl, 3-chloro-4-methylphenyl, 2-cyanophenyl, 2-methoxy-5-chlorophenyl and 3,4-methylenedioxyphenyl. R is preferably phenyl, 2-fluorophenyl, 2-chlorophenyl or 2-methoxyphenyl.

The group $R^1$ in Formula I above is a furanyl group, a thienyl group or a group of the formula

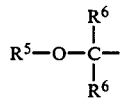

wherein $R^5$ is lower-cycloalkyl, lower-alkyl, halogenated lower-alkyl, phenyl or phenyl lower-alkyl, and wherein each $R^6$ is independently selected from hydrogen, lower-cycloalkyl or lower-alkyl. The furanyl or thienyl groups can be attached to the carbonyl carbon at the 2 or 3 position of the ring. Examples of suitable $R^1$ groups include methoxymethyl, ethoxymethyl, 1-propoxymethyl, 2-propoxymethyl, 1-butoxymethyl, 1-pentoxymethyl, 1-hexoxymethyl, cyclohexoxymethyl, 1-heptoxymethyl, 1-methoxyethyl, 1-ethoxy-1-ethyl, 1-butoxy-1-ethyl, phenoxymethyl, benzyloxymethyl, 2,2,2-trifluoroethoxymethyl, 2-furanyl, 3-furanyl, 3-thienyl and 2-thienyl. A preferred $R^1$ group is methoxymethyl, 1-methoxyethyl, 2-furanyl, 3-furanyl or 2-thienyl.

$R^2$ is Formula I above is selected from the group consisting of phenyl lower-alkyl, lower-alkyl, lower-alkenyl, lower-alkynyl, halogenated lower-alkyl, (cycloalkyl)alkyl, thienyl lower-alkyl, thiazolyl lower-alkyl which can be substituted in the 4-position with a methyl group, (4,5-dihydro-5-oxo-1H-tetrazol-1-yl) lower-alkyl which can be substituted in the 4-position with a group selected from lower-alkyl, lower-cycloalkyl, aryl or aryl lower-alkyl, and substituted phenyl lower-alkyl in which the substituents on the phenyl ring are selected from halogen, cyano, lower-alkoxy, lower-alkyl, lower-alkylenedioxy, halogenated lower-alkyl, lower-alkylthio or combinations thereof. Suitable $R^2$ groups include benzyl, 2-phenylethyl, 2-(4-fluorophenyl)ethyl, 2-(2-fluorophenyl)ethyl, 1-phenylethyl, 1-phenyl-2-propyl, 2-phenyl-1-propyl, 2-(4-ethyl-4,5-dihydro-5-oxo-1H-tetrazol-1-yl)ethyl, 2-(4-benzyl-4,5-dihydro-5-oxo-1H-tetrazol-1-yl)ethyl, 2-(4-phenyl-4,5-dihydro-5-oxo-1H-tetrazol-1-yl)ethyl, 2-(4-cyclopentyl- 4,5-dihydro-5-oxo-1H-tetrazol-1-yl)ethyl, 2-(4-methyl-thiazol-5-yl)ethyl, 2-(2-thienyl)ethyl, 2-(3-thienyl)ethyl, 3-methyl-1-butyl, 1-methyl-1-butyl, 2-methyl-1-propyl, 1-heptyl, cyclopentylmethyl, 2,2,2-trifluoroethyl, 2-butynyl, 2-propenyl, and 2-methyl-2-propenyl. 2-Phenylethyl, 1-phenyl-2-propyl, 2-phenyl-1-propyl, and 2-(2-thienyl)ethyl are preferred $R^2$ groups.

The $R^3$ group in Formula I is selected from the group consisting of hydrogen, methoxymethyl, and a carboxylate radical represented by the formula:

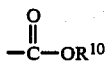

In the carboxylate radical, $R^{10}$ is selected from the group consisting of lower alkyl, aryl-lower-alkyl, lower-alkoxy-lower alkyl or aryloxy-lower-alkyl. Suitable $R^3$ groups include hydrogen, methoxymethyl, methoxycarbonyl, benzyloxycarbonyl, 2-phenylpropoxy carbonyl, 2-phenoxyethoxy carbonyl, 2-methoxyethoxy carbonyl, and 2-phenylethoxy carbonyl. Preferred $R^3$ groups are hydrogen, methoxymethyl and methoxycarbonyl.

By lower-alkyl, lower-alkenyl, and lower-alknyl groups, we mean branched or unbranched groups containing from 1 to 7 carbon atoms. Also, by lower-cycloalkyl groups, we intend to include such groups containing from 3 to 6 carbon atoms. Preferred aryl groups include from 6 to 12 carbon atoms and can include any of the substituents discussed above in connection with the phenyl rings.

The compounds of the present invention can be prepared by various methods. In general, the desired compounds of Formula I above can be prepared by reacting a compound of the formula

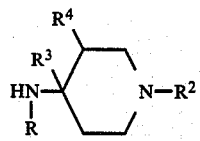

with a compound of the formula

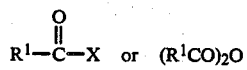

or by reacting a compound of the formula

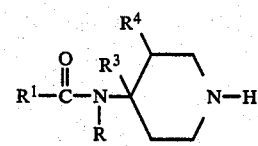

with a compound of the formula $R^2X$ wherein R, $R^1$, $R^2$, $R^3$ and $R^4$ have the meanings given above and X represents halide or its reactive equivalent. Examples include toluene, sulfonate, phenyl sulfonate and methyl sulfonate. In the former reaction with $R^2$ being benzyl or phenylethyl, the benzyl or phenylethyl group can be split off and replaced with other $R^2$ group such as 2(2-thienyl)ethyl, (4-methyl-thiazol-5-yl) ethyl, etc.

Several convenient routes for the preparation of the compounds of the invention begin with known piperidones (1) and (2) below:

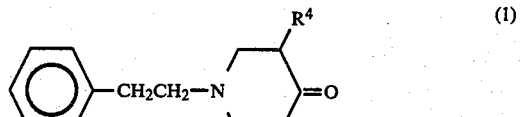

or

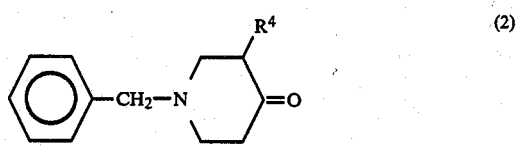

1-(2-phenylethyl)-4-piperidone or 1-(2-phenylethyl)-3-methyl-4-piperidone (compound 1) can be prepared according to the procedure published by A. H. Becket, A. F. Casey and G. Kirk, *J. Med. Pharm. Chem.*, Vol. 1, 37 (1959). N-benzyl-4-piperidone or N-benzyl-3-methyl-4-piperidone (compound 2) can be prepared in an analogous manner by the procedures described by C. R. Ganellin and R. G. Spickch, *J. Med. Chem.*, Vol. 8, 619 (1965) or P. M. Carabateas and L. Grumbach, *J. Med. Pharm. Chem.*, Vol. 5, 913 (1962).

In one example of a process of the invention, 1-benzyl or 1-(2-phenylethyl)-4-piperidone may be reacted with aniline or a substituted aniline and the resulting Schiff base may be reduced with, for example, sodium borohydride to give 1-benzyl or 1-(2-phenylethyl)-4-phenylaminopiperidine or the corresponding substituted phenyl compound if substituted aniline is employed. The following reaction scheme illustrates such a method:

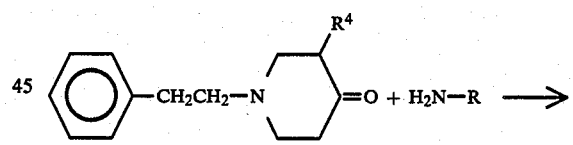

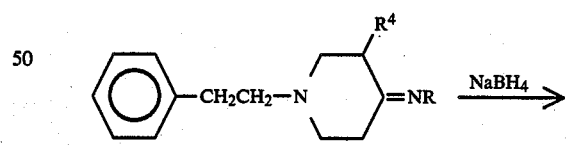

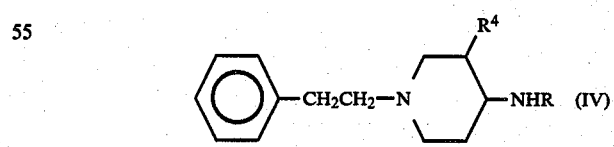

When $R^4$ is hydrogen, the compound IV can be reacted with the appropriate acid halide (e.g., $R^1COCl$) or anhydride [$(R^1CO)_2O$] to introduce the $R^1$—CO— group on the amino nitrogen. When $R^4$ is methyl, there are cis or trans isomers created. Thus, the cis and trans isomers can be separated before or after reaction with an acid halide or anhydride, e.g., according to the following reaction scheme:

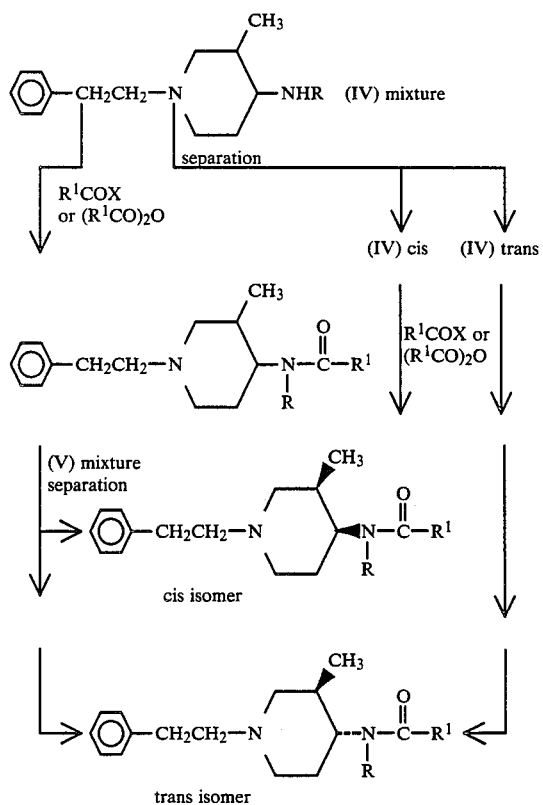

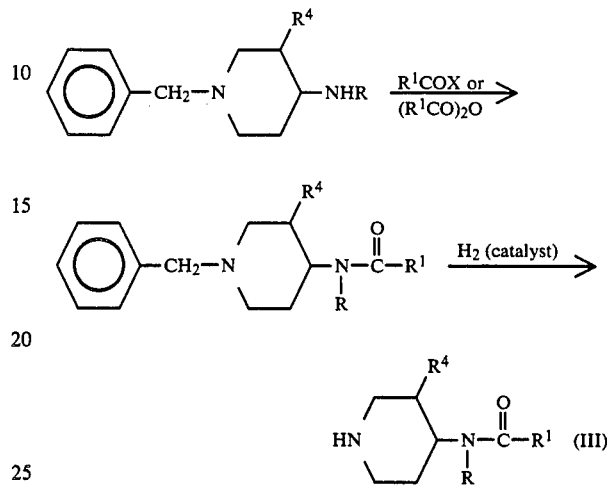

When the final desired $R^2$ is not phenylethyl, one procedure for preparing the compounds of the invention is to start with compound 2 above and subsequently split off the benzyl group and replace it with the desired $R^2$ group. For example, the compounds of the invention can be prepared by the following reaction scheme:

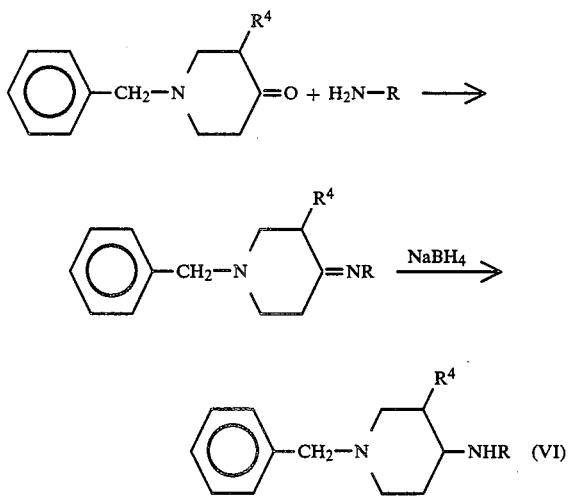

When $R^4$ is methyl, compound VI consists of a mixture of cis and trans isomers which can be separated prior to the next reaction step. When $R^4$ is hydrogen, no preliminary cis/trans separation need be employed. After any such separation into cis or trans isomer, the compound (VI) can be reacted in the following reaction scheme to provide first a piperidinyl intermediate III:

The appropriate $R^2$ group can then be introduced by reacting the compound of formula III with an appropriately reactive molecule $R^2$—X wherein X is, for example, halogen such as chlorine, bromine or iodine, e.g., as illustrated below:

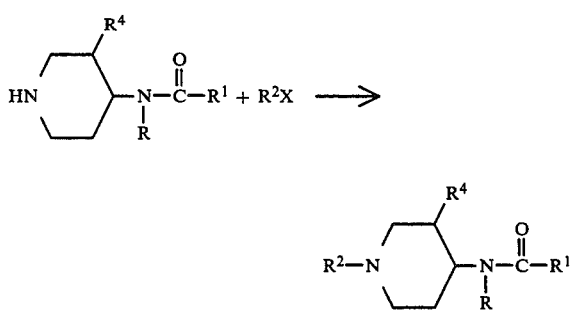

The reaction of $R^2$—X with a piperidinyl intermediate such as the compound of the formula III can be conducted in an inert organic solvent such as, for example, an aromatic hydrocarbon; a ketone, e.g., 4-methyl-2-pentanone and the like; an ether, e.g., 1,4-dioxane, diethylether, tetrahydrofuran, 1,2-dimethoxyethane and the like; or N,N-dimethylformamide. The addition of an appropriate base, such as an alkali metal carbonate, may be utilized to neutralize the acid liberated during the course of the reaction. The addition of an iodide salt, such as an alkali metal iodide, may be appropriate. Elevated temperature may be employed to increase the rate of reaction where appropriate.

Alternatively, starting with the compound of the formula VI, the benzyl group could be first split off prior to separation of the cis/trans e.g., by one of the two schemes below:

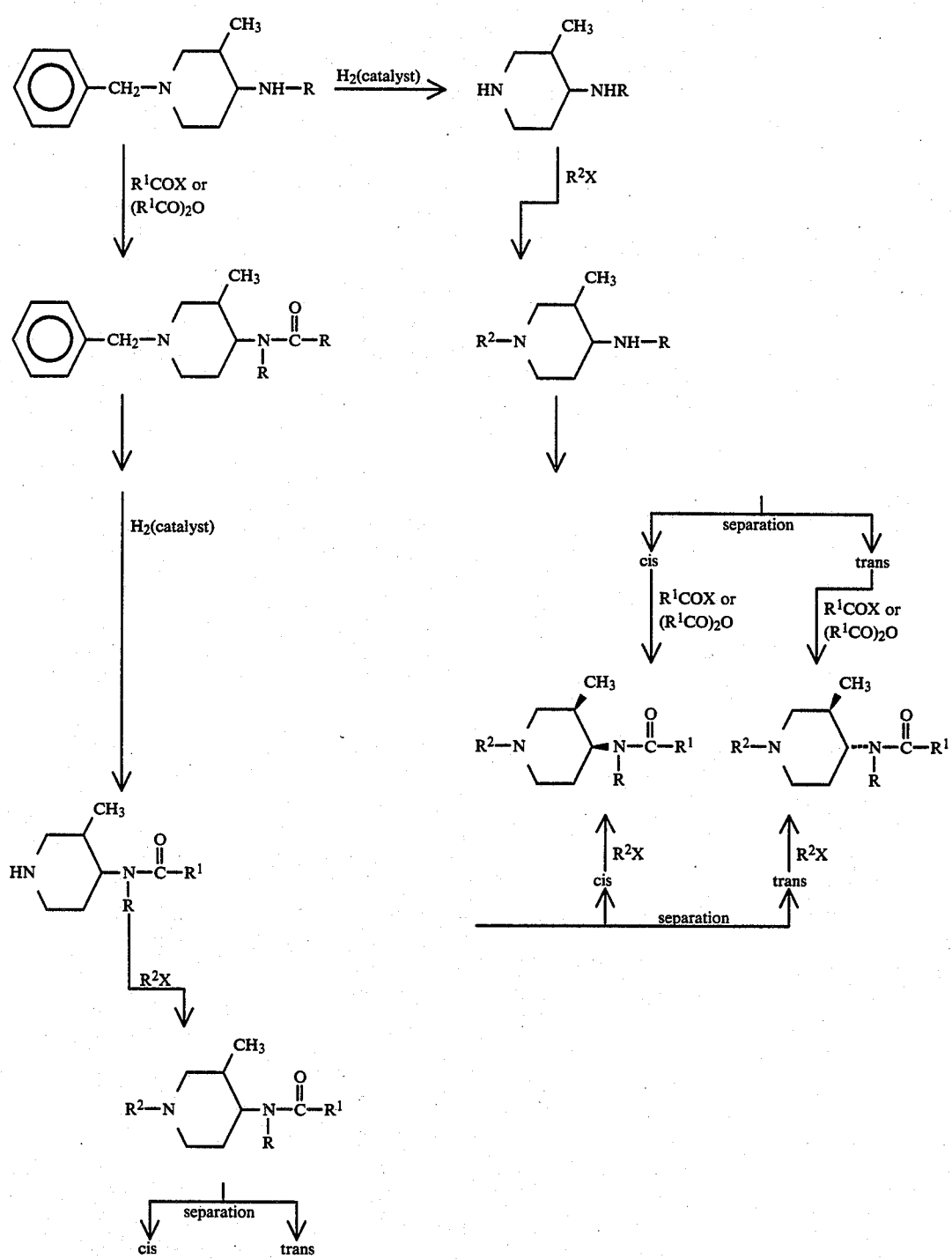
Compounds of the invention having 4,4-disubstitution can also be prepared starting with, for example, N-benzyl-4-piperidone by the following reaction schemes:
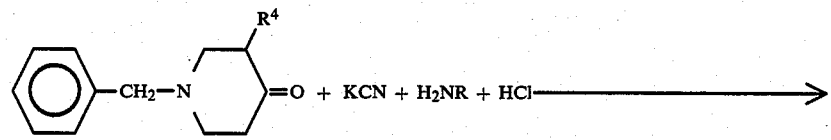

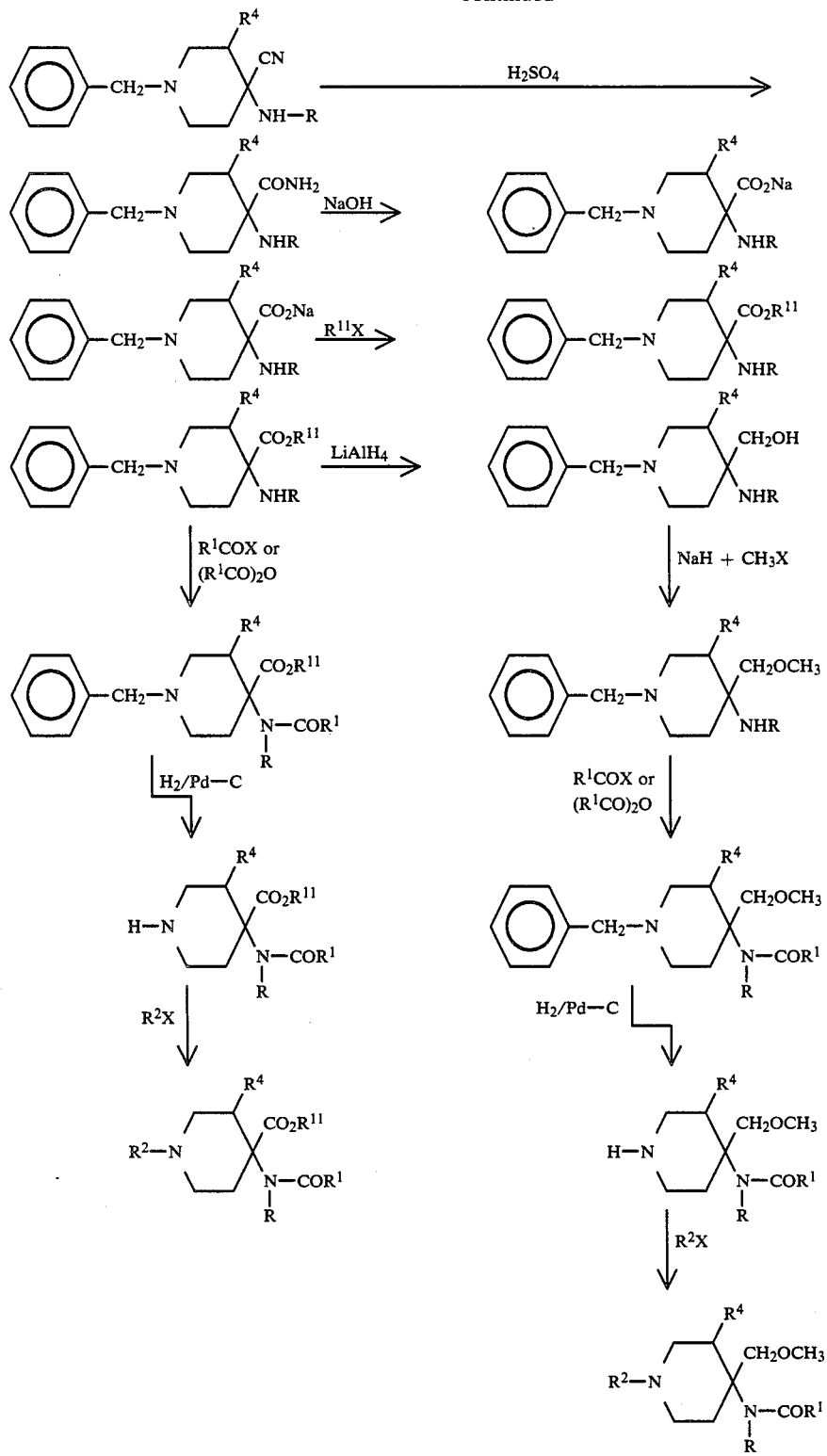

wherein $R^{11}$ can be $R^{10}$ if the desired end product is a 4—$CO_2R^{10}$ group but can be another alkyl, arylalkyl, etc. group if conversion to a methoxymethyl group is to be carried out.

The compounds of the invention can exist in the form of the free base or the therapeutically or pharmaceutically acceptable acid addition salts by treatment with an appropriate acid, such as an inorganic acid, e.g., hydrochloric, hydrobromic, sulfuric, nitric, phosphoric acids and the like; or an organic acid such as acetic, trifluoroacetic, propionic, hydroxyacetic, methoxyacetic, benzoic, citric, oxalic, methanesulfonic, ethanesulfonic, benzenesulfonic, toluenesulfonic, succinic, tartaric, and the like acids. Preferred acid addition salts are the chloride and citrate. These acid addition salts can be prepared by conventional methods, e.g., by treatment with the appropriate acid.

Compounds of the invention having at least one assymetric carbon atom can exist in optically active iosmeric forms. For example, in compounds in which $R^2$ is a 2-phenyl-1-propyl or 1-phenyl-2-propyl group, etc., the carbon adjacent to the piperidinyl nitrogen is an assymetric carbon and such compounds can therefore exist in optical active isomeric (enantiomeric) forms. Such isomeric forms can be isolated from the racemic mixtures by techniques known to those skilled in the art.

The compounds of the inventions having methyl as the $R^4$ groups exist in cis or trans form. Such compounds can be used as a mixture of such forms but many times one form is more active than the other or has other desirable characteristics. Thus, many times it is desirable to resolve the cis/trans mixture. This can be accomplished by techniques conventional in the art for such purpose, e.g., chromatographic techniques such as column chromatography or high pressure liquid chromatography or by simple recrystallization.

The compounds of the invention, prepared as the free base, can be combined with a pharmaceutically acceptable carrier to provide a pharmaceutical composition. Suitable carriers for the free bases include propylene glycol-alcohol-water, isotonic water, sterile water for injection, USP, emulphor TM -alcohol-water, cremophor-EL TM or other carriers known to those skilled in the art.

The compounds of the invention prepared as the pharmaceutically acceptable acid addition salts can also be combined with a pharmaceutically acceptable carrier to provide a pharmaceutical composition. Suitable carriers for the acid addition salts may include an isotonic aqueous solution, or sterile water for injection, USP, alone or in combination with other solubilizing agents such as ethanol, propylene glycol, or other conventional solubilizing agents known to those skilled in the art. Of course, the carrier will vary depending upon the mode of administration desired for the pharmaceutical composition as is conventional in the art. A preferred carrier is an isotonic aqueous solution containing from 0.0001 mg/ml to 0.5 mg/ml of at least one of the compounds of this invention depending upon the pharmacology of the individual compounds being employed in the formulation.

The compounds of the invention can be administered to mammals, e.g., animals or humans, in amounts effective to provide the desired analgesic effect. The compounds can be administered intravenously, intramuscularly or subcutaneously in the previously described carriers. These compounds may also be administered orally, sublingually, rectally, or transcutaneously with a suitable pharmaceutically acceptable carrier for that mode of administration as is conventional in the art.

As noted above, an effective amount of the compounds of the present invention is employed to obtain the desired analgesic effect. Since the activity of the compounds and the depth of the desired analgesia or anesthesia vary, the dosage level employed of the compound also varies. The actual dosage administered will be determined by such generally recognized factors as the body weight of the patient or the idiosyncrasies of the particular patient. Thus, the unit dosage for a particular patient (man) can be as low as 0.00005 mg/Kg, which the practitioner may titrate to the desired effect.

A number of compounds of the present invention, when used in conjunction with inhalation anesthetics such as isoflurane (available under the tradename Forane from BOC) and enflurane (available under the tradename Ethrane from BOC) reduces the minimum alveolar concentration of the inhalation anesthetic needed to produce surgical levels of anesthesia.

The following examples are presented for purposes of demonstrating, but not limiting the compounds or compositions of this invention.

EXAMPLE I

A mixture of 20.3 g 1-(2-phenylethyl)-4-piperidone, 10.8 g of aniline, 0.1 g of toluene sulfonic acid, and 80 ml of toluene is heated to and maintained at reflux in an apparatus containing a Dean-Stark trap to collect water. When the calculated amount of water is collected, the mixture is cooled and toluene is removed by flash evaporation. The residue is dissolved in 100 ml of methanol and 3.8 g of sodium borohydride is added in small portions. The mixture is maintained at reflux for one hour. Water, 50 ml, is added dropwise. The mixture is flash evaporated to remove methanol. An additional 30 ml of water is added and the product is extracted three times with 100 ml of toluene. The toluene extracts are combined, washed with 30 ml of water three times, dried over anhydrous sodium sulfate, and flash evaporated to yield 22.9 g of an oil. The oil is dissolved in 18 ml of toluene and chromatographed on a Waters Associated Prep. LC/System 500, using a PrepPAK-500/SILICA column and 50% ethyl acetate/50% hexane. The main fraction is collected and flash evaporated under vacuo. The residue is recrystallized from petroleum ether to give 1-(2-phenylethyl)-4-(N-phenylamino)piperidine, m.p. 96°–98° C.

EXAMPLE II

Following the procedure of Example I above and using an equivalent amount of 2-chloroaniline instead of aniline provides 1-(2-phenylethyl)-4-[N-(2-chlorophenyl)amino]piperidine, as an oil.

EXAMPLE III

To 1.35 g of 1-(2-phenylethyl)-4-(N-phenylamino)-piperidine in 20 ml of dimethoxyethane, 0.6 g of methoxyacetyl chloride is added and stirred for two days. The precipitate is collected, recrystallized from 2-propanol and dried in vacuo at 65° C. to give 1.2 g of 1-(2-phenylethyl)-4-(N-phenylmethoxyacetamido)-piperidinium chloride, m.p. 214°–215° C.

EXAMPLE IV

When an equivalent amount of ethoxyacetyl chloride is substituted for methoxyacetyl chloride in the procedure of Example III, 1-(2-phenylethyl)-4-(N-phenylethoxyacetamido)piperidinium chloride, m.p. 213°–214° C., is isolated after recrystallization from 2-propanol/diisopropyl ether.

EXAMPLE V

When an equivalent amount of 2-furoyl chloride is substituted for methoxyacetyl chloride in the procedure of Example III, 1-(2-phenylethyl)-4-(N-phenyl-2-furoylamido)piperidinium chloride is isolated, m.p. 235° C. (decomp.).

EXAMPLE VI

When an equivalent amount of 1-(2-phenylethyl)-4-[N-(2-chlorophenyl)amino]piperidine is substituted for 1-(2-phenylethyl)-4-(N-phenylamino)piperidine in Example III, 1-(2-phenylethyl)-4-[N-(2-chlorophenyl)methoxyacetamido]piperidinium chloride, m.p. 196°–197° C., is isolated.

EXAMPLE VII

When an equivalent amount of 2-methoxypropionyl chloride is substituted for methoxyacetyl chloride in the procedure of Example III, 1-(2-phenylethyl)-4-(N-phenyl-2-methoxypropionamido)piperidinium chloride, m.p. 204°–205° C. (decomp.), is prepared in good yield.

EXAMPLE VIII

Aniline, 60 g (1 mole), 95 g of 1-benzyl-4-piperidone (1 mole) and 1 g of p-toluenesulfonic acid are dissolved in 700 ml of toluene, then heated to and maintained at a reflux in an appropriate apparatus containing a Dean-Stark trap to collect water. When the calculated amount of water is collected, the mixture is cooled and the toluene is removed by flash evaporation. The residue is dissolved in 600 ml of methanol and 23 g of sodium borohydride is added in small portions. The mixture is left stirring overnight. Then 300 ml of water is added to the reaction mixture. The methanol is flash evaporated and the residue is extracted three times with 300 ml of toluene. The toluene extracts are combined, washed three times with 200 ml of water, and dried over sodium sulfate. The toluene is flash evaporated. The resulting oil is allowed to crystallize. The crystals are collected, washed with 2-propanol and dried, then recrystallized two time from hexane. Additional fractions of crystals are collected in a similar fashion to yield 64%, m.p. 85.5°–87° C., of 1-benzyl-4-(N-phenylamino)piperidine.

EXAMPLE IX

Replacing aniline in the procedure of Example VIII with an equivalent amount of 4-fluoroaniline results in a 50% yield of 1-benzyl-4-[N-(4-fluorophenyl)amino]piperidine, m.p. 90°–91° C.

EXAMPLE X

To 600 ml of dry toluene, 66.5 g of 1-benzyl-4-(N-phenylamino)piperidine and 27 g of methoxyacetyl chloride are added and allowed to stir for two days. The precipitate is collected, washed with acetone, and recrystallized from 2-propanol to give 1-benzyl-4-(N-phenylmethoxyacetamido)piperidine hydrochloride in 64% yield, m.p. 224.5°–225.5° C. To 26 g of the previously prepared amide in 100 ml of ethanol, 3 g of 5% palladium on carbon is added and the reaction mixture is placed on a Parr hydrogenation apparatus. The solution is left agitating for two days and the calculated amount of hydrogen is consumed. The catalyst is removed by filtration. Ethanol is removed by flash evaporation. The residue is crystallized from 2-propanol to yield 95% 4-(N-phenylmethoxyacetamido)piperidinium chloride, m.p. 219°–220° C.

EXAMPLE XI

In an appropriate apparatus with a reflux condenser and a nitrogen atmosphere, 50 ml of diethyl ether is added to 5.5 g (0.23 moles) of freshly scratched magnesium turnings. Then 100 g (0.21 moles) of 2-bromothiophene is diluted with 200 ml of diethyl ether and 100 ml of this solution is added to the flask containing the magnesium turnings. When the reaction begins to reflux, a cooling bath is used to moderate the reaction. When the reaction slows down, aliquots of the thiophene solution are added to maintain a steady reflux rate. After all of the thiophene solution is added, the reaction is stirred overnight. The next day an aliquot of a solution is prepared from 100 g of 2-chloroethyl p-toluene sulfonate and 100 ml of diethyl ether is added to the Grignard reagent and the reaction mixture is warmed to reflux until it becomes turbid. Additional aliquots are added intermittantly until all of the tosylate is added. The mixture is refluxed for nine hours, cooled, 100 g of ice is added, and then aqueous HCl (120 ml conc. HCl diluted with 500 ml of water) is added. The ether layer is removed. The aqueous layer is extracted two times with diethyl ether. The ether layers are combined and washed two times with water. The ether solution is dried over 50 g of sodium sulfate. The ether is flash evaporated and the residue is vacuum distilled at 1 mm, $bp_{1\ mm} = 50°–51.5°$ C., to yield 9.7 g of 2-chloroethyl-2-thiophene.

EXAMPLE XII

A mixture of 5 g of 4-(N-phenylmethoxyacetamido)piperidinium chloride, 0.4 g of 2-chloroethyl-2-thiophene, 9 g of sodium carbonate, 0.5 g of potassium iodide, and 100 ml of 4-methyl-2-pentanone are combined, stirred with a magnetic stirring bar, and heated to reflux for 17 hours. The reaction mixture is cooled, 200 ml of water added, and the organic phase is removed by separation. The aqueous portion is extracted with toluene. The toluene layer and the organic phase are combined, dried and flash evaporated. The residual oil is dissolved in ethyl acetate and passed through a silica gel column (prepared with ethyl acetate). Seven 200 ml fractions are collected. Each fraction is flash evaporated. Fraction 3 is shaken with 100 ml of diisopropyl ether and filtered. On standing, crystallization takes place. The crystals from the filtrate of fraction 3 are collected, dried, and 0.9 g is dissolved in 10 ml of hot 2-propanol. Then 0.49 g of citric acid is dissolved in another 10 ml portion of hot 2-propanol; the two 2-propanol solutions are combined and left to crystallize. The crystals are collected and vacuum dried, yielding 1-[2-(2-thienyl)ethyl]-4-(N-phenylmethoxyacetamido)piperidinium citrate, m.p. 155° C. (decomp.).

EXAMPLE XIII

Substituting 1-phenyl-2-bromopropane for 2-chloroethyl-2-thiophene in the procedure of Example XII gives 1-(2-phenyl-1-propyl)-4-(N-phenylmethoxyacetamido)piperidinium citrate, m.p. 142° C. (decomp.).

EXAMPLE XIV

Combining 1-phenyl-2-bromopropane with 4-[N-(4-fluorophenyl)methoxyacetamido]piperidine in the procedure similar to that of Example XII the base 1-(2-phenyl-1-propyl)-4-[N-4-fluorophenyl)methoxyacetamido]piperidine is formed. Dry HCl is added to a toluene solution of the base to obtain 1-(2-phenyl-1-propyl)-4-[N-(4-fluorophenyl)methoxyacetamido]piperidinium chloride, m.p. 250° C.

EXAMPLE XV

To a stirred solution of 36.5 g of 1-benzyl-4-(N-phenylamino)-4-(methoxycarbonyl)piperidine in 200 ml of toluene, 14.6 g of methoxyacetyl chloride is added, followed by 22 ml of triethylamine. The reaction mixture is stirred for 5 days and 100 ml of 10% sodium hydroxide is added. After stirring overnight, the product is extracted with toluene, dried and flash evaporated to yield 51.1 g of an oil. The 1-benzyl-4-methoxycarbonyl-4-(N-phenylmethoxyacetamido)piperidine is separated from the starting material using a Waters Associates Prep LC/System 500 and a PrepPAK-500/SILICA column (1:1 ethyl acetate:hexane). THe pure fraction is collected and the eluent is evaporated to give 1-benzyl-4-methoxycarbonyl-4-(N-phenylmethoxyacetamido)piperidine.

A mixture of 12.45 g of 1-benzyl-4-methoxycarbonyl-4-(N-phenylmethoxyacetamido)piperidine and 250 ml of acetic acid is hydrogenated at room temperature and pressure with 1.5 g of 10% palladium-on-charcoal catalyst. After the calculated amount of hydrogen is taken up, the catalyst is filtered off. The acetic acid is flash evaporated, the residue is dissolved in toulene and stirred with 10 g of anhydrous sodium carbonate. The solid is filtered and the filtrate is flash evaporated to obtain 4-methoxycarbonyl-4-(N-phenylmethoxyacetamido)piperidine.

A mixture of 1 g of 4-methoxycarbonyl-4-(N-phenylmethoxyacetamido)piperidine, 0.12 sodium iodine, 3.5 g of sodium carbonate, 0.47 g of 2-chlroethylbenzene and 50 ml of methyl isobutyl ketone is maintained at reflux for six days. The mixture is cooled, diluted with 500 ml of toluene and washed three times with 20 ml of water. The organic phase is dried over 20 g of sodium sulfate. The solid is filtered off and the solvent flash evaporated to give an oil. The oil is purified using a Waters Associates Prep LC/System 500 and a PrePAK-500/SILICA column (ethyl acetate). A yield of 0.51 g of 1-(2-phenylethyl)-4-methoxycarbonyl-4-(N-phenylmethoxyacetamido)piperidine is isolated, combined with 0.06 g of oxalic acid in methanol and heated to reflux. Methyl t-butyl ether is added dropwise to the refluxing solution until a cloud point is reached. Additional methonol is added to the cloudy refluxing solution until it clears. The solution is cooled and the precipitate collected via filtration. The precipitate is dried under vacuo to give 0.46 g of 1-(2-phenylethyl)-4-methoxycarbonyl-4-(N-phenylmethoxyacetamido)piperidinium oxalate, m.p. 170°–172° C. (decomp.).

EXAMPLE XVI

A stirred solution of 76.1 g of methyl 1-benzyl-4-anilino-4-piperidine carboxylate in 1200 ml of toluene is maintained at ambient temperature while 130 ml of a 70% solution of sodium dihydrobis(2-methoxyethoxy)aluminate in benzene is added dropwise. Stirring is continued for one hour after the addition. Two hundred grams of a saturated solution of sodium sulfate is added. The aqueous portion is removed and the organic portion is dried over sodium sulfate and flash evaporated to give 72.5 g of 1-benzyl-4-anilino-4-piperidinemethanol, as an oil.

A mixture of 72.5 g of 1-benzyl-4-anilino-4-piperidinemethanol, 11 g of sodium hydride (50% in mineral oil) and 427 g of hexamethylphosphoric triamide is stirred. Then 33 g of methyl iodide is added dropwise to the reaction mixture and the mixture is stirred overnight. The mixture is added to 2500 ml of water, extracted with six 500 ml portions of toluene, dried over anhydrous sodium sulfate and flash evaporated to give an oil. The oil is purified in a Waters Associates Prep LC/System 500, using a PrepPAK-500/SILICA column (40% ethyl acetate in hexane) to give 1-benzyl-4-methoxymethyl-4-anilinopiperidine.

A mixture of 9.75 g of 1-benzyl-4-methoxymethyl-4-anilinopiperidine, 3 g of methoxyacetyl chloride, 9 ml of triethylamine and 80 ml of toluene is stirred at ambient conditions for 4 days. An additional 3 g of methoxyacetyl chloride is added, stirred for 1 day and left to stand for three days. To the reaction mixture, 22 ml of 10% sodium hydroxide and 80 ml toluene are added with stirring. The organic layer is separated, washed five times with 50 ml portions of water, dried over sodium sulfate and flash evaporated to give an oil. The oil is purified using a Waters Associates Prep LC/System 500, and a PrepPAK-500/SILICA column (30% hexane in ethyl acetate) to give 8.12 g of 1-benzyl-4-methoxymethyl-4-(N-phenylmethoxyacetamido)piperidine.

In a fashion similar to the hydrogenation procedure of Example XV, 6 g of 1-benzyl-4-methoxymethyl-4-(N-phenylmethoxyacetamido)piperidine is hydrogenated to give an oil, 2.7 g of which is purified by a silica gel column. Ethyl acetate is used as the mobile phase. An ethyl acetate solution of the oil is put on the column and 300 ml of ethyl acetate is passed through the column. The mobile phase is changed to methanol and 300 ml of eluent is collected and flash evaporated to give 2.6 g of 4-methoxymethyl-4-(N-phenylmethoxyacetamido)piperidine.

A mixture of 0.67 g of 4-methoxymethyl-4-(N-phenylmethoxyacetamido)piperidine, 0.1 g of sodium iodide, 2.4 g of sodium carbonate, 3.9 g of (2-chloroethyl)benzene and 75 ml of methyl isobutyl ketone is heated to and maintained at a reflux for four days. The reaction mixture is cooled and filtered. The filtrate is evaporated and the resulting oil is purified using a Waters Associates Prep LC/System 500 and a PrepPAK-500/SILICA column. The mobile phase is 5% methanol in ethyl acetate. The eluent is flash evaporated to give 0.42 g of 1-(2-phenylethyl)-4-methoxymethyl-4-(N-phenylmethoxyacetamido)piperidine.

A mixture of 0.24 g of 1-(2-phenylethyl)-4-methoxymethyl-4-(N-phenylmethoxyacetamido)piperidine, 0.06 g of oxalic acid and 50 ml of methanol is heated to reflux. Methyl-t-butyl ether is added dropwise to the boiling reaction mixture until a cloud point is reached. Additional methanol is added to clear the mixture. The solution is cooled, the crystals of 1-(2-phenylethyl)-4-methoxymethyl-4-(N-phenylmethoxyacetamido)piperidinium oxalate are collected by suction filtration and dried under vacuo, 0.23 g, m.p. 180°–181° C. (decomp.).

EXAMPLE XVII

A mixture of 0.79 g of a 4-methoxymethyl-4-(N-phenylmethoxyacetamido)piperidine, 0.4 g of 2-chloroethyl-2-thiophene, 0.19 g of sodium iodide, 3 g of sodium carbonate and 50 ml of methyl i-butyl ketone is heated to and maintained at a reflux for 4 days. The reaction mixture is cooled and filtered. The filtrate is evaporated and the resulting oil is purified on a 25 mm × 100 mm silica-gel chromatography column using ethyl acetate as the mobile phase. The fractions are collected and flash evaporated. The fraction containing the desired compound yields 0.72 g of an oil, 0.58 g of which is added to a solution of 0.14 g of oxalic acid in 50 ml of methanol and heated to and maintained at a reflux. Then methyl t-butyl ether is added dropwise to the refluxing mixture until a cloud point is reached. Additional methanol is added until the mixture clears. The solution is cooled to room temperature and 0.58 g of crystals are collected, recrystallized from 2-propanol/methyl t-butyl ether and dried in vacuo. A yield of 0.54 g of 1-[2-(2-thienyl)ethyl]-4-methoxymethyl-4-(N-phenylmethoxyacetamido)piperidinium oxalate, m.p. 183°–184° C. (decomp.), is obtained.

EXAMPLE XVIII

Following the procedure of Example XVII and using an equivalent quantity of 1-(2-chloroethyl)-4-ethyl-1,4-dihydro-5-H-tetrazol-5-one instead of 2-chloroethyl-2-thiophene gives 1-[2-(4-ethyl-4,5-dihydro-5-oxo-1H-tetrazol-1-yl)ethyl]-4-methoxymethyl-4-(N-phenylmethoxyacetamido)piperidine which is purified on a Waters Associates Prep LC/System 500, using a Prep-PAK-500/SILICA column (5% methanol in ethyl acetate). The resulting oil is combined with oxalic acid as described in Example XV and pure 1-[2-(4-ethyl-4,5-dihydro-5-oxo-1H-tetrazol-1-yl)ethyl]-4-methoxymethyl-4-(N-phenylmethoxyacetamido)piperidinium oxalate, m.p. 140°–141° C., is obtained.

EXAMPLE XIX

When an equivalent amount of 2-chloroethyl-2-thiophene is substituted for 2-chloroethylbenzene in Example XV, 1-[2-(2-thienyl)ethyl]-4-methoxycarbonyl-4-(N-phenylmethoxyacetamido)piperidinium oxalate is isolated, m.p. 190°–191° C. (decomp.).

EXAMPLE XX

When an equivalent amount of 1-(2-chloroethyl)-4-ethyl-1,4-dihydro-5-H-tetrazol-5-one is substituted for 2-chloroethylbenzene in Example XV, 1-[2-(4-ethyl-4,5-dihydro-5-oxo-1H-tetrazol-1-yl)ethyl]-4-methoxycarbonyl-4-(N-phenylmethoxyacetamido)piperidinium oxalate is isolated, m.p. 172°–173° C. (decomp.).

EXAMPLE XXI

When an equivalent amount of a 1-bromo-2-phenylpropane is substituted for 2-chloroethylbenzene in Example XV, 1-(2-phenyl-1-propyl)-4-methoxycarbonyl-4-(N-phenylmethoxyacetamido)piperidinium oxalate is isolated, m.p. (hemihydrate) 90°–91° C.

EXAMPLE XXII

A mixture of 1.0 g of 4-methoxycarbonyl-4-[N-(2-fluorophenyl)methoxyacetamido]piperidine, 1.34 g of 1-iodo-2-methylpropane, 3.39 g of sodium carbonate and 30 ml of ethyl acetate is heated to and maintained at reflux for three days. The reaction mixture is cooled and filtered. The filtrate is evaporated in vacuo. The residue is chromatographed on silica-gel with a mixture of ethyl acetate and hexane (7/3 volume/volume) as the eluting solvent. Fractions containing the desired compound are combined and evaporated to obtain 0.51 g of white crystals. To this is added 0.121 g of oxalic acid, and the mixture is dissolved in a minimum amount of boiling acetone. The solution is cooled to room temperature and filtered. A yield of 0.27 g of 1-(2-methylpropyl)-4-methoxycarbonyl-4-[N-(2-fluorophenyl)methoxyacetamido]piperidinium oxalate, m.p. 189°–190° C., is obtained.

EXAMPLE XXIII

Twenty-five grams of N-benzyl-3-methyl-4-piperidone, 23.25 g of 2-fluoroaniline and a catalytic amount of p-toluenesulfonic acid are heated at reflux in 350 ml of toluene, with the removal of water. After the calculated amount of water (2.2 ml) is collected, the reaction is cooled to room temperature and the solvent is evaporated. The remaining heavy oil is then diluted with 250 ml of methanol, 19 g of NaBH4 are added slowly to the reaction, and it is stirred at room temperature overnight. After removal of the methanol, the solid is dissolved in water and extracted 3 times with 150 ml of toluene. The organic layer is dryed over MgSO4. After removal of the solvent, the product, 1-benzyl-3-methyl-4-(2-fluoroanilino)piperidine, is vacuum distilled at 0.1 mm Hg, 140°–170° C., with a yield of 53%.

EXAMPLE XXIV

Ten grams of 1-benzyl-3-methyl-4-(2-fluorophenylanilino)piperidine from Example XXIII and 4.0 g of methoxyacetylchloride are mixed in 130 ml of dry tetrahydrofuran. After two days of refluxing at room temperature, the product thereof is converted to the free base (10% NaOH) and 12 g of 1-benzyl-3-methyl-4-[N-(2-fluorophenyl)methoxyacetamido]piperidine is obtained (99% yield).

EXAMPLE XXV

Twelve grams of the isomeric mixture of Example XXIV is dissolved in 50 ml of ethanol. To this solution 0.5 g of 10% Pd on carbon is added and the whole reaction is put in a Parr Apparatus for 18 hours. The catalyst is filtered and after removal of the solvent, the product is purified by chromatography on a dry packed silica gel column using methanol/NH4OH (1:0.5% v:v) as the mobile phase (Rf~0.2). A yield of 3.2 g (45% yield) of 3-methyl-[N-(2-fluorophenyl)methoxyacetamido]piperidine is obtained.

EXAMPLE XXVI

Potassium carbonate (11.9 g), 3-methyl-4-[N-(2-fluorophenyl)methoxyacetamido]piperidine (2.42 g), 1-(2-chloroethyl)-4-ethyl-1,4-dihydro-5H-tetrazol-5-one (1.68 g), and few crystals of potassium iodide are heated at reflux in 4-methyl-2-pentanone overnight. The reaction is cooled to room temperature and the solid 1-[2-(4-ethyl-4,5-dihydro-1H-tetrazol-yl)ethyl]-3-methyl-4-[N-(2-fluorophenyl)methoxyacetamido]piperidine is dissolved in water and extracted with toluene. After drying the organic phase, the solvent is removed and the isomers (cis/trans) are separated by column chromatography using 100% ethyl acetate as the mobile phase. In this way, 1.2 g of pure cis, upper spot (Rf~0.3), and 0.75 g of trans, lower spot (Rf~0.24), are obtained. The combined total yield is 56%. The cis compound is converted to its oxalate salt (m.p. 151°–153° C.), using the procedure outlined at the end of Example 22.

EXAMPLE XXVII

Ten grams of 1-benzyl-3-methyl-4-(2-fluoroanilino)piperidine of Example XXIII and 4.57 g of 2-methoxypropionyl chloride are mixed in dry tetrahydrofuran. After two weeks the solid product is filtered from the mixture and converted with 10% NaOH to the free base; 10 g of 1-benzyl-3-methyl-4-[N-(2-fluorophenyl)-

2-methoxypropionamido]piperidine is obtained (90% yield).

EXAMPLE XXVIII

Ten grams of the amide of Example XXVII are dissolved in ethanol and 0.7 g of 10% Pd on carbon is added to the reaction. The hydrogenolysis is carried out under pressure in a Parr apparatus. The progress of the reaction is monitored by TLC. The reaction is completed after two days. The catalyst is then removed by filtration and the solvent is evaporated. At this point the product, 3-methyl-4-[N-(2-fluorophenyl)-2-methoxypropionamido]piperidine, is separated into two distinct forms: 2 g formed a crystalline compound (Rf=0.18) which is the trans form and 2.2 g remained as an oil (Rf=0.34) which is the cis form.

EXAMPLE XXIX

The cis-compound with Rf value 0.34 from Example XXVIII (2.2 g), 2-(2-thienyl)ethyl chloride (1.2 g), potassium carbonate (11.05 g) and few crystals of potassium iodide are heated at reflux in 150 ml of 4-methyl-2-pentanone. After two days the reaction is cooled to room temperature and the solvent is flash evaporated. The solid residue is dissolved in water and extracted 2 times with 75 ml of toluene. After drying the organic layer with MgSO$_4$, the solvent is flash evaporated and the product is purified by column chromatography using 100% ethyl acetate as the mobile phase. A yield of 1.23 g of 1-[2-(2-thienyl)ethyl]-3-methyl-4-[N-(2-fluorophenyl)-2-methoxypropionamido]piperidine (Rf=0.23) is obtained (41% yield). The compound is converted to its oxalate salt (m.p. 203°-204° C.), using the procedure outlined at the end of Example 22.

EXAMPLE XXX

A number of compounds in accordance with the present invention were tested for their analgesic properties. Specifically, the acid addition salts of the compounds tested in accordance with the invention were dissolved in sterile water for injection, USP, to form a solution whose concentration may vary from 0.00001 mg/ml to 5 mg/ml. The solution was administered intravenously in a mouse tail vein. The ED$_{50}$ values were obtained from the mouse hot plate analgesia test (58° C.) described in Domer, Floyd R., *Animal Experiments in Pharmacological Analysis*, Charles C. Thomas, Springfield, 1971, p. 283 ff. The compounds listed in Table 1 below were tested by this procedure and found to have the activities listed in the right hand column of Table 1.

TABLE 1

| COMPOUND | M.P. °C. | Analgesic Activity (ED/50) mg/Rg Mice |
| --- | --- | --- |
| 1-(2-phenylethyl)-4-(N—phenylmethoxyacetamido)piperidinium chloride | 214–215 | 0.08 |
| 1-(2-phenylethyl)-4-[N—(4-chlorophenyl)methoxyacetamido]piperidinium chloride | 232–234 | 0.5 |
| 1-(2-phenylethyl)-4-(N—phenylethoxyacetamido)piperidinium chloride | 213–214 | 0.7 |
| 1-(2-phenylethyl)-4-[N—(4-chlorophenyl)ethoxyacetamido]piperidinium chloride | 225–227 | >1.0 |
| 1-(3-phenyl-2-propyl)-4-(N—phenylmethoxyacetamido)piperidinium chloride | 244–246 | 0.04 |
| 1-[2-(2-thienyl)ethyl]-4-(N—phenylmethoxyacetamido)piperidinium chloride | 99–103 | 0.004 |
| 1-(2-phenylethyl)-4-(N—phenyl-2-furoylamido)piperidinium chloride | 235 (dec.) | 0.02 |
| 1-(2-phenylethyl)-4-(N—phenyl-2-methoxypropionamido)piperidinium oxalate | 175–176 | 0.3 |
| 1-(2-phenylethyl)-4-[N—(4-chlorophenyl)-2-methoxypropionamido]piperidinium chloride | 220–222 | 2.5 |
| 1-[2-(2-thienyl)ethyl]-4-[N—(3,4-methylenedioxyphenyl)methoxyacetamido]piperidinium chloride | 122–123.5 | 0.3 |
| 1-(2-phenylethyl)-4-[N—(2-chlorophenyl)-2-methoxypropionamido]piperdinium chloride | 213–217 | 0.08 |
| 1-[2-(2-thienyl)ethyl]-4-[N—(3-chloro-4-methylphenyl)methoxyacetamido]piperidinium chloride | 122–124 | 0.5 |
| 1-(2-phenylethyl)-4-[N—(2-methoxy-3-chlorophenyl)-2-methoxypropionamido]piperidinium chloride | 161–168 | 1.4 |
| 1-(2-phenylethyl)-4-[N—(2-chlorophenyl)methoxyacetamido]piperidinium oxalate | 173–174 | 0.04 |
| 1-(1-phenyl-2-propyl)-4-[N—(3,4-methylenedioxyphenyl)methoxyacetamido]piperidinium chloride | 215 | 0.2 |
| 1-(2-phenyl-1-propyl)-4-[N—(3,4-methylenedioxyphenyl)methoxyacetamido]piperidinium chloride | 208–210 | 0.3 |
| 1-[2-(2-thienyl)ethyl]-4-[N—(4-chlorophenyl)methoxyacetamido]piperidinium chloride | 116–118 | 0.4 |
| 1-(2-phenyl-1-propyl)-4-[N—(4-fluorophenyl)methoxyacetamido]piperidinium chloride | 221–222 | 0.2 |
| 1-(1-phenyl-2-propyl)-4-[N—(4-fluorophenyl)methoxyacetamido]piperidinium chloride | >250 | 0.05 |
| 1-[2-(2-thienyl)ethyl]-4-(N—phenylmethoxyacetamido)piperidinium oxalate | 190–191 | 0.0007 |
| 1-(2-phenylethyl)-4-methoxycarbonyl-4-(N—phenylmethoxyacetamido)piperidinium oxalate | 170–172 | 0.003 |
| 1-(2-phenylethyl)-4-methoxymethyl-4-(N—phenylmethoxyacetamido)piperidinium oxalate | 180–181 | 0.005 |
| 1-[2-(2-thienyl)ethyl]-4-methoxymethyl-4-(N—phenylmethoxyacetamido)piperidinium oxalate | 183–184 (dec.) | 0.004 |
| 1-(2-phenylethyl)-4-[N—(2-methoxyphenyl)methoxyacetamido]piperidinium chloride | 206–207 | 0.1 |
| 1-(2-phenylethyl)-4-[N—(2-methoxyphenyl)2-methoxypropionamido]- | 233 | 0.2 |

TABLE 1-continued

| COMPOUND | M.P. °C. | Analgesic Activity (ED/50) mg/Rg Mice |
|---|---|---|
| piperidinium chloride | | |
| 1-[2-(4-ethyl-4,5-dihydro-5-oxo-1H—tetrazol-1-yl)ethyl]-4-methoxycarbonyl-4-(N—phenylmethoxyacetamido)piperidinium oxalate | 172–173 (dec.) | 1.6 |
| 1-[2-(4-ethyl-4,5-dihydro-5-oxo-1H—tetrazol-1-yl)ethyl]-4-methoxymethyl-4-(N—phenylmethoxyacetamido)piperidinium oxalate | 140–141 | 1.1 |
| 1-(2-phenyl-1-propyl)-4-methoxycarbonyl-4-(N—phenylmethoxyacetamido)piperidinium oxalate | 144–145 | 0.004 |
| 1-(2-phenyl-1-propyl)-4-(N—phenylmethoxyacetamido)-piperidinium chloride | 185–192 | 0.084 |
| 1-benzyl-4-[N—(2,6-dimethylphenyl)methoxyacetamido]-piperidinium chloride | 198–204 | 3.5 |
| 1-(2-phenylethyl)-4-[(N—phenyl)-2-ethoxypropionamido]-piperidinium chloride | 185–187 | 0.75 |
| 1-benzyl-4-[N—(3-chloro-4-methoxyphenyl)methoxyacetamido]-piperidinium chloride | 254–255 | 2.2 |
| 1-(2-phenylethyl)-4-[N—(3-chlorophenyl)methoxyacetamido]-piperidinium chloride | 230–231 | 2.1 |
| 1-(2-phenylethyl)-4-[N—(3-chlorophenyl)-2-methoxypropionamido]-piperidinium chloride | 202–214 | 8.0 |
| 1-(2-phenyl-1-propyl)-4-[N— (3-chloro-4-methylphenyl)methoxyacetamido]piperidinium chloride | 172–175 | 2.2 |
| 1-[2-(2-thienyl)ethyl]-4-(N—phenyl-2-methoxypropionamido)-piperidine | 96–100 | 0.35 |
| 1-(2-phenyl-1-propyl)-4-(N—phenyl-2-methoxypropionamido)-piperidinium chloride | 116–118 | 0.50 |
| 1-(2-phenylethyl)-4-[N—(2-methoxyphenyl)-2,2,2-trifluoroethoxyacetamido]piperidinium chloride | 204–205 | 3.0 |
| 1-(2-phenylethyl)-4-[N—(2-methoxyphenyl)ethoxyacetamido]piperidinium chloride | 202–203 | 1.2 |
| 1-(2-phenylethyl)-4-[N—(2-methoxyphenyl)-2-propoxyacetamido]-piperidinium chloride | 213–214 | 4.1 |
| 1-(2-phenylethyl)-4-[N—(2-methoxy-5-chlorophenyl)-2-methoxypropionamido]piperidinium chloride | 238 (decomp.) | 0.38 |
| 1-(2-phenylethyl)-4-[N—(2-methoxy-5-chlorophenyl)-2-ethoxypropionamido]piperdinium chloride | 211–215 | 0.63 |
| 1-(2-phenylethyl)-4-[N—(2-chlorophenyl)ethoxyacetamido]piperidinium chloride | 172–174 | 0.22 |
| 1-(2-phenylethyl)-4-[N—(2-chlorophenyl)-2,2,2-trifluoroethoxyacetamido]piperidinium chloride | 194–196 | 4.8 |
| 1-(2-phenylethyl)-4-[N—(2-methoxy-5-chlorophenyl)-2-furoylamido]piperidinium oxalate | 218 (decomp.) | 0.032 |
| 1-(2-phenylethyl)-4-[N—phenyl-(1-butoxy-2-propionamido)]-piperidinium citrate | 136–138 | 2.0 |
| 1-(2-phenylethyl)-4-[N—(3-methoxyphenyl)benzyloxyacetamido]piperidinium citrate | 142–143 | 2.8 |
| 1-(2-phenylethyl)-4-[N—(2-methoxy-5-chlorophenyl)ethoxyacetamido]piperidinium citrate | 143 | 2.7 |
| 1-(2-phenylethyl)-4-[N—(2-methoxy-5-chlorophenyl)methoxyacetamido]piperidinium citrate | 211–212 | 0.43 |
| 1-(2-phenylethyl)-4-[N—(2-methoxyphenyl)-1-butoxy-2-propionamido]piperidinium citrate | 178–179 | 1.1 |
| 1-(2-phenylethyl)-4-[N—(2-chlorophenyl)ethoxypropionamido]piperidinium oxalate | 210–212 | 0.093 |
| 1-(2-phenylethyl)-4-[N—(2-methoxyphenyl)-3-furoylamido] piperidinium oxalate | 194–195 | 0.046 |
| 1-(2-phenylethyl)-4-[N—(2-methoxy-phenyl)-2-furoylamido]piperidinium oxalate | 212 | 0.014 |
| 1-(2-phenylethyl)-4-[N—(2-chlorophenyl)-3-furoylamido]piperidinium oxalate | 179 | 1.8 |
| 1-(2-phenylethyl)-4-[N—(2-chlorophenyl)-2-furoylamido]piperidinium oxalate | 185–186 | 0.068 |
| 1-(2-phenylethyl)-4-[N—(3-chloro-4-methoxyphenyl)methoxyacetamido]-piperidinium chloride | 231–232 | 2.8 |
| 1-(2-phenylethyl)-4-[N—(3-chloro-4-methoxyphenyl)cyclohexyloxyacetamido]-piperidinium chloride | 205–206 | 7.9 |
| 1-(2-phenylethyl)-4-[N—(3-chloro-4-methoxyphenyl)ethoxyacetamido]-piperidinium chloride | 224–225 | 7.8 |
| 1-(2-phenylethyl)-4-[N—(2-trifluoromethylphenyl)methoxyacetamido]-piperidinium oxalate | 165–167 | 0.65 |
| 1-(2-phenylethyl)-4-[N—(2-methylthiophenyl)methoxyacetamido]-piperidinium oxalate | 188–190 | 2.0 |
| 1-(2-phenylethyl)-4-[N—(2-trifluoromethylphenyl)-2-furoylacetamido]-piperidinium oxalate | 177–178 | 7.2 |
| 1-(2-phenylethyl)-4-[N—(2-trifluoromethylphenyl)-1-propoxyacetamido]-piperdinium oxalate | 174 | 7.2 |
| 1-(2-phenylethyl)-4-[N—(2-trifluoromethylphenyl)ethoxyacetamido]-piperidinium oxalate | 171–172 | 2.1 |
| 1-(2-phenylethyl)-4-[N—(2-fluorophenyl)methoxyacetamido]piperidinium oxalate | 183–184 | 0.0077 |

TABLE 1-continued

| COMPOUND | M.P. °C. | Analgesic Activity (ED/50) mg/Rg Mice |
|---|---|---|
| 1-(2-phenylethyl)-4-[N—(2-fluorophenyl)-2-methoxypropionamido]-piperidinium oxalate | 184–185 | 0.068 |
| 1-(2-phenylethyl)-4-[N—(2-fluorophenyl)-2-furoylamido]piperidinium oxalate | 211 | 5.0 |
| 1-(2-phenylethyl)-4-[N—(3-chloro-4-methoxyphenyl)-2-ethoxypropionamido]-piperidinium chloride | 197–200 | 0.29 |
| 1-(2-phenylethyl)-4-[N—(3,4-methylenedioxyphenyl)-3-furoylamido]-piperidinium oxalate | 197–198 | 2.1 |
| 1-(2-phenylethyl)-4-[N—(3-chloro-4-methoxyphenyl)-2-furoylamido]-piperidinium oxalate | 208–210 | 1.8 |
| 1-(2-phenylethyl)-4-[N—(3-chloro-4-methoxyphenyl)-3-furoylamido]-piperidinium oxalate | 204–205 | 2.2 |
| 1-(2-phenylethyl)-4-(N—phenyl)-3-furoylamido]piperidinium oxalate | 197 (dec) | 0.076 |
| 1-[2-(2-thienyl)ethyl]-4-[N—(2-methoxyphenyl)methoxyacetamido]-piperidinium oxalate | 175 | 0.046 |
| 1-(2-phenylethyl)-4-[N—(3-chloro-4-methoxyphenyl)-2-methoxypropionamido]-piperidinium chloride | 233–235 | 2.0 |
| 1-(2-phenylethyl)-4-[N—(2-methylthiophenyl)ethoxyacetamido]-piperidinium oxalate | 186–187 | 1.6 |
| 1-(2-phenylethyl)-4-[N—(2-methylthiophenyl)-2-propoxyacetamido]-piperidinium oxalate | 192–193 | 5.4 |
| 1-(2-phenyl-1-propyl)-4-[N—(2-methoxyphenyl)methoxyacetamido]-piperidinium oxalate | 170 | 0.1 |
| 1-(2-phenylethyl)-4-[N—(2-fluorophenyl)-3-furoylamido]-piperidinium oxalate | 187–188 | 0.069 |
| 1-[2-(3-thienyl)ethyl]-4-(N—phenylmethoxyacetamido)piperidinium oxalate | 202–203 | 0.1 |
| 1-[2-(4-methylthiazol-5-yl)ethyl]-4-(N—phenylmethoxyacetamido)-piperidinium oxalate | 176–177 | 1.9 |
| 1-(2-phenylethyl)-4-[N—(2-methylthiophenyl)-2-methoxypropionamido]-piperidinium oxalate | 196–197 | 0.58 |
| 1-(1-phenyl-2-propyl)-4-[N—(2-methoxyphenyl)methoxyacetamido]-piperidinium chloride | 203–204 | 0.08 |
| 1-(2-phenylethyl)-4-[N—(2-fluorophenyl)ethoxyacetamido]-piperidinium oxalate | 187–189 | 0.25 |
| 1-(2-phenylethyl)-4-[N—(2-fluorophenyl)-2-thiophenecarboxamide]-piperidinium oxalate | 214–214.5 | 0.17 |
| 1-(2-phenylethyl)-4-[N—(2-fluorophenyl)methoxyacetamido]piperidinium oxalate | 181–182 | 0.019 |
| 1-[2-(4-methylthiazol-5-yl)ethyl]-4-[N—(2-fluorophenyl)methoxyacetamido]-piperidinium oxalate | 172–174 | 0.16 |
| 1-[2-(2-fluorophenyl)ethyl]-4-[N—(2-fluorophenyl)methoxyacetamido]-piperidinium oxalate | 168–169 | 0.0089 |
| 1-[2-(4-fluorophenyl)ethyl]-4-[N—(2-fluorophenyl)methoxyacetamido]-piperidinium oxalate | 175–177 | 0.085 |
| 1-[2-(3-thienyl)ethyl]-4-[N—(2-fluorophenyl)methoxyacetamido]-piperidinium oxalate | 187–188 | 0.014 |
| 1-(2-methylpropyl)-4-[N—(2-fluorophenyl)methoxyacetamido]-piperidinium chloride | 184–185 | 1.7 |
| 1-(2-phenyl-1-propyl)-4-[N—(2-fluorophenyl)methoxyacetamido]-piperidinium chloride | 164–165 | 0.056 |
| 1-(2-phenylethyl)-4-[N—(2-fluorophenyl)phenoxyacetamido]-piperidinium oxalate | 182–183 | 2.2 |
| 1-(2-phenylethyl)-4-[N—(2-fluorophenyl)benzyloxyacetamido]-piperidinium oxalate | 165–166 | 3.5 |
| 1-[2-(2-thienyl)ethyl]-4-[N—(2-ethylphenyl)-2-methoxypropionamido]-piperidinium oxalate | 181–182 | 5.0 |
| 1-(2-phenylethyl)-4-[N—(2-cyanophenyl)-2-methoxypropionamido]-piperidinium oxalate | 203–204 | 0.55 |
| 1-(2-phenylethyl)-4-[N—(2-fluorophenyl)-2-propoxyacetamido]-piperidinium oxalate | 187–188 | 2.8 |
| 1-(2-phenylethyl)-4-[N—(2-trifluoromethylphenyl)-2-propoxyacetamido]-piperidinium oxalate | 183–184 | 5.0 |
| 1-[2-(2-thienyl)ethyl]-4-[N—(2-ethylphenyl)methoxyacetamido]-piperidinium oxalate | 156–157 | 1.4 |
| 1-(3-methyl-1-butyl)-4-methoxymethyl-4-(N—phenylmethoxyacetamido)-piperidinium oxalate | 165–166 | 0.21 |
| 1-benzyl-4-methoxycarbonyl-4-(N—phenylmethoxyacetamido)-piperidinium oxalate | 164–166 | 0.82 |
| 1-(3-methyl-1-butyl)-4-methoxycarbonyl-4-(N—phenylmethoxyacetamido)-piperidinium oxalate | 159 | 0.024 |
| 1-(2-methyl-1-propyl)-4-methoxycarbonyl-4-(N—phenylmethoxyacetamido)-piperidinium oxalate | 181 | 0.015 |
| 1-[(2-(3-thienyl)ethyl]-4-methoxycarbonyl-4-(N—phenylmethoxyacetamido)-piperidinium oxalate | 180 | 0.0036 |
| 1-(2-phenyl-1-propyl)-4-methoxycarbonyl-4-(N—phenylmethoxyacetamido)-piperidinium oxalate | 144–145 | 0.065 |
| 1-benzyl-4-methoxycarbonyl-4-[N—(2-fluorophenyl)methoxyacetamido]-piperidinium oxalate | 191–192 | 0.23 |

TABLE 1-continued

| COMPOUND | M.P. °C. | Analgesic Activity (ED/50) mg/Rg Mice |
|---|---|---|
| 1-(2-methyl-1-propyl)-4-methoxycarbonyl-4-[N—(2-fluorophenyl)-methoxyacetamido]piperidinium oxalate | 189–190 | 0.0048 |
| 1-[2-(2-thienyl)ethyl]-3-methyl-4-(N—phenyl-2-methoxypropionamido)-piperidinium oxalate | 218–219 | 0.012 |
| 1-[2-(2-thienyl)ethyl]-3-methyl-4-(N—phenyl-2-furoylamido)-piperidinium oxalate | 203–204 | 0.0047 |
| 1-[2-(2-thienyl)ethyl]-3-methyl-4-(N—phenylmethoxyacetamido)-piperidinium chloride | 172–174 | 0.0011 |
| 1-(2-phenylethyl)-3-methyl-4-[N—(2-fluorophenyl)-2-furoylamido]-piperidinium oxalate | 195–196 | 0.33 |
| 1-(2-phenylethyl)-3-methyl-4-[N—(2-fluorophenyl)methoxyacetamido]-piperidinium chloride | 196–202 | 0.0011 |
| 1-(2-phenylethyl)-3-methyl-4-[N—(2-fluorophenyl)-2-methoxypropionamido]piperidinium chloride | 208–212 | 0.014 |
| 1-(2-phenylethyl)-3-methyl-4-[N—(2-methoxyphenyl)-2-furoylamido]-piperidinium oxalate | 203–204 | 0.088 |
| 1-(2-phenylethyl)-3-methyl-4-[N—(2-methoxyphenyl)benzyloxyacetamido]-piperidinium chloride | 164–167 | 6. |
| 1-(2-phenylethyl)-3-methyl-4-[N—(2-methoxyphenyl)-2-methoxypropionamido]-piperidinium chloride | 219–221 | 1.4 |
| 1-(2-phenylethyl)-3-methyl-4-(N—phenylmethoxyacetamido)-piperidinium chloride | 187–188 | 0.071 |
| 1-(2-phenylethyl)-3-methyl-4-[(N—phenyl)-2-furoylamido]-piperidinium chloride | 176–183 | 0.044 |
| 1-(2-phenylethyl)-3-methyl-4-[(N—phenyl)-2-methoxypropionamido]-piperidinium chloride | 199–205 | 0.158 |
| trans-1-(2-phenylethyl)-3-methyl-4-[N—(2-methoxyphenyl)methoxyacetamido]-piperidine | 166–168 | 0.11 |
| 1-(2-phenylethyl)-3-methyl-4-[(N—phenyl)phenoxyacetamido]piperidinium oxalate | 108–111 | 2.2 |
| 1-[2-(2-thienyl)ethyl]-3-methyl-4-[N—(2-methoxyphenyl)methoxyacetamido]-piperidinium chloride | 105–109 | 0.55 |
| 1-[2-(2-thienyl)ethyl]-3-methyl-4-[N—(2-methoxy-phenyl)furoylamido]-piperidinium oxalate | 188–192 | 0.079 |
| 1-[2-(2-thienyl)ethyl]-3-methyl-4-[N—(2-fluorophenyl)methoxyacetamido]-piperidinium oxalate | 176–179 | 0.0011 |
| cis-1-[2-(2-thienyl)ethyl]-3-methyl-4-[N—(2-fluorophenyl)-2-methoxypropionamido] piperidinium oxalate | 204–205 | 0.0057 |
| cis-1-[2-(2-thienyl)ethyl]-3-methyl-4-(N—phenylmethoxyacetamido)-piperidinium oxalate | 161–163 | 0.0017 |
| cis-1-[2-(2-thienyl)ethyl]-3-methyl-4-(N—phenyl-2-methoxypropionamido)-piperidinium oxalate | 217–218 | 0.02 |
| cis-1-[2-(2-thienyl)ethyl]-3-methyl-4-[N—(2-fluorophenyl)methoxyacetamido]-piperidinium oxalate | 185–186 | 0.00056 |
| trans-1-[2-(2-thienyl)ethyl]-3-methyl-4-[N—(2-fluorophenyl)methoxyacetamido]-piperidinium oxalate | 155–156 | 0.0027 |
| cis-1-[2-(4-ethyl-4,5-dihydro-5-oxo-1H—tetrazol-1-yl)ethyl]-3-methyl-4-(N—phenyl-2-methoxypropionamido)piperidinium oxalate | 147–148 | 6 |
| cis-1-[2-(4-ethyl-4,5-dihydro-5-oxo-1H—tetrazol-1-yl)ethyl]-3-methyl-4-(N—phenylmethoxyacetamido)piperidinium oxalate | 145–146 | 1.5 |
| 1-[2-(4-ethyl-4,5-dihydro-5-oxo-1H—tetrazol-1-yl)ethyl]-3-methyl-4-[N—(2-fluorophenyl)methoxyacetamido]piperidinium oxalate | 148–150 | 0.13 |
| cis-1-[2-(4-ethyl-4,5-dihydro-5-oxo-1H—tetrazol-1-yl)ethyl]-3-methyl-4-[N—(2-fluorophenyl)methoxyacetamido)piperidinium oxalate | 151–153 | 0.098 |
| cis-1-[2-(2-thienyl)ethyl]-3-methyl-4-[N—(2-fluorophenyl)-2-methoxypropionamido]piperidinium oxalate | 203–204 | 0.0051 |
| trans-1-[2-(2-thienyl)ethyl]-3-methyl-4-[N—(2-fluorophenyl)-2-furoylamido]-piperidinium oxalate | 168–169 | 0.021 |
| trans-1-[2-(4-ethyl-4,5-dihydro-5-oxo-1H—tetrazol-1-yl)ethyl]-3-methyl-4-[N—(2-fluorophenyl)-2-furoylamido]piperidinium oxalate | 174–175 | 8 |
| cis-1-(2-phenylethyl)-3-methyl-4-[N—(2-methoxyphenyl)methoxyacetamido]piperidinium chloride | 175–176 | 0.29 |
| trans-1-(2-phenylethyl)-3-methyl-4-[N—(2-methoxyphenyl)methoxyacetamido]piperidinium oxalate | 202–204 | 0.17 |
| cis-1-[2-(4-ethyl-4,5-dihydro-5-oxo-1H—tetrazol-1-yl)ethyl]-3-methyl-4-[N—(2-fluorophenyl)-2-furoylamido]piperidinium oxalate | 154–156 | 0.3 |
| cis-1-(2-phenylethyl)-3-methyl-4-[ N—(2-chlorophenyl)methoxyacetamido]-piperidinium oxalate | 171–175 | 0.078 |
| trans-1-(2-phenylethyl)-3-methyl-4-[N—(2-methoxyphenyl)-2-furoylamido]-piperidinium oxalate | 227–229 | 0.12 |
| cis-1-(2-phenylethyl)-3-methyl-4-[N—(2-chlorophenyl)-2-furoylamido]-piperidinium oxalate | 200–202 | 10. |
| trans-1-(2-phenylethyl)-3-methyl-4-[N—(2-chlorophenyl)-2-furoylamido]-piperidinium oxalate | 187–189.5 | 0.25 |
| trans-1-benzyl-3-methyl-4-(N—phenyl-2-methoxypropionamido)-piperidinium oxalate | 183–184 | 5 |
| cis-1-(2-phenylethyl)-3-methyl-4-(N—phenyl-2-methoxypropionamido)-piperidinium oxalate | 204–205 | 0.035 |
| cis-1-(2-phenylethyl)-3-methyl-4-(N—phenylmethoxyacetamido)-piperidinium oxalate | 135–136 | 0.0016 |

TABLE 1-continued

| COMPOUND | M.P. °C. | Analgesic Activity (ED/50) mg/Rg Mice |
|---|---|---|
| trans-1-[2-(4-ethyl-4,5-dihydro-5-oxo-1H—tetrazol-1-yl)ethyl]-3-methyl-4-[N—(2-fluorophenyl)-2-methoxypropionamido]piperidinium oxalate | 206–209 | 2.5 |
| cis-1-[2-(2-thienyl)ethyl]-3-methyl-4-[N—(2-methoxyphenyl)methoxyacetamido]piperidinium chloride | 194–195 | 0.9 |
| cis-1-benzyl-3-methyl-4-(N—phenyl-2-furoylamido)piperidinium oxalate | 190–191 | 4 |
| cis-1-[2-(2-thienyl)ethyl]-3-methyl-4-[N—(2-methoxyphenyl)-2-furoylamido]piperidinium oxalate | 195–195.5 | 0.57 |
| cis-1-[2-(2-thienyl)ethyl]-3-methyl-4-[N—(2-fluorophenyl)-2-furoylamido]piperidinium oxalate | 191–192 | 0.004 |
| trans-1-[2-(2-thienyl)ethyl]-3-methyl-4-[(N—phenyl)-2-methoxypropionamido]piperidinium oxalate | 180–181 | 0.024 |
| cis-1-(2-phenylethyl)-3-methyl-4-[N—(2-chlorophenyl)-2-methoxypropionamido]piperidinium oxalate | 212–213 | 0.67 |
| trans-1-(2-phenylethyl)-3-methyl-4-[N—(2-chlorophenyl)-2-methoxypropionamido]piperidinium oxalate | 171–172 | 0.0048 |
| cis-1-(2-phenylethyl)-3-methyl-4-[N—(2-fluorophenyl)methoxyacetamido]piperidinium oxalate | 168–169 | 0.0041 |
| trans-1-(2-phenylethyl)-3-methyl-4-[N—(2-methoxyphenyl)-2-methoxypropionamido]piperidinium oxalate | 223–226 | 0.65 |
| trans-1-(2-phenylethyl)-3-methyl-4-[N—(2-fluorophenyl)-2-methoxypropionamido]piperidinium oxalate | 197–198 | 0.01 |
| trans-1-(2-phenylethyl)-3-methyl-4-[N—(2-fluorophenyl)methoxyacetamido]piperidinium oxalate | 180–181 | 0.00069 |
| trans-1-(2-phenylethyl)-3-methyl-4-(N—phenylmethoxyacetamido)piperidinium oxalate | 180–181 | 0.041 |

EXAMPLE XXXI

Other compounds also prepared include:

1-(2-phenyl-1-propyl)-4-methoxycarbonyl-4-(n-phenylmethoxyacetamido)piperidinium oxalate (m.p. 205°–206° C.)

1-[2-(3-thienyl)ethyl]-4-methoxycarbonyl-4-[N-(2-fluorophenyl)methoxyacetamido]piperidinium oxalate (m.p. 177°–178° C.)

1-(2-phenyl-1-propyl)-4-methoxycarbonyl-4-[N-(2-fluorophenyl)methoxyacetamido]piperidinium oxalate (m.p. 144°–146° C.)

1-(2-phenylethyl)-4-(2-phenylethoxycarbonyl)-4-[N-(2-fluorophenyl)methoxyacetamido]piperidinium oxatate (m.p. 170°–172° C.)

1-[2-(2-thienyl)ethyl]-4-methoxycarbonyl-4-[N-(2-fluorophenyl)methoxyacetamido]piperidinium oxalate (m.p. 190° C.)

1-[2-(4-methylthiazol-5-yl)ethyl]-4-methoxycarbonyl-4-[N-(2-fluorophenyl)methoxyacetamido]piperidinium oxalate (m.p. 186°–187° C.)

1-(2-phenylethyl)-4-methoxycarbonyl-4-[N-(2-fluorophenyl)methoxyacetamido]piperidinium oxalate (m.p. 190° C.)

1-[2-(4-ethyl-4,5-dihydro-5-oxo-1H-tetrazol-1-yl)ethyl]-4-methoxycarbonyl-4-[N-(2-fluorophenyl)methoxyacetamido]piperdinium oxalate (m.p. 148°–149° C.)

1-[2-(4-ethyl-4,5-dihydro-5-oxo-1H-tetrazol-1-yl)ethyl]-4-methoxycarbonyl-4-[N-(2-methoxyphenyl)methoxyacetamido]piperidinium oxalate (m.p. 158°–161° C.)

1-(2-methyl-1-propyl)-4-methoxycarbonyl-4-[N-(2-methoxyphenyl)methoxyacetamido]piperidinium oxalate (m.p. 190° C.) (decomp.)

1-(3-methyl-1-butyl)-4-methoxycarbonyl-4-[N-(2-methoxyphenyl)methoxyacetamido]piperidinium oxalate (m.p. 180°–181° C.)

1-(1-methyl-1-butyl)-4-methoxycarbonyl-4-[N-(2-methoxyphenyl)methoxyacetamido]piperidinium oxalate (m.p. 140°–142° C.)

1-benzyl-4-methoxycarbonyl-4-[N-(2-methoxyphenyl)methoxyacetamido]piperidinium oxalate (m.p. 204°–205° C.)

1-(1-phenylethyl)-4-methoxycarbonyl-4-[N-(2-methoxyphenyl)methoxyacetamido]piperidinium oxalate (m.p. 100°–102° C.)

1-(2-phenylethyl)-4-methoxycarbonyl-4-[N-(2-methoxyphenyl)methoxyacetamido]piperidinium oxalate (m.p. 198°–199° C.)

1-(2-phenyl-1-propyl)-4-methoxycarbonyl-4-[N-(2-methoxyphenyl)methoxyacetamido]piperidinium oxalate (m.p. 135°–137° C.)

1-[2-(2-thienyl)ethyl]-4-methoxycarbonyl-4-[N-(2-methoxyphenyl)methoxyacetamido]piperidinium oxalate (m.p. 202° C.)

1-[2-(3-thienyl)ethyl]-4-methoxycarbonyl-4-[N-(2-methoxyphenyl)methoxyacetamido]piperidinium oxalate (m.p. 201° C.)

1-[2-(4-methylthiazol-5-yl)ethyl]-4-methoxycarbonyl-4-[N-(2-methoxyphenyl)methoxyacetamido]piperidinium oxalate (m.p. 170°–172° C.)

trans-1-(2-phenylethyl)-3-methyl-4-(N-phenyl-2-methoxypropionamido)piperidinium oxalate (m.p. 167°–169° C.)

cis-1-(2-phenylethyl)-3-methyl-4-[N-(2-fluorophenyl)-2-methoxypropionamido]piperidinium oxalate (m.p. 179°–180° C.)

trans-1-(2-phenylethyl)-3-methyl-4-[N-(2-chlorophenyl)-2-methoxypropionamido]piperidinium oxalate (m.p. 138°–140° C.)

cis-1-(2-phenylethyl)-3-methyl-4-[(N-phenyl)-2-furoylamido]piperidinium oxalate (m.p. 177°–178° C.)

trans-1-(2-phenylethyl)-3-methyl-4-[(N-phenyl)-2-furoylamido]piperidinium oxalate (m.p. 169°–170° C.)

cis-1-[2-(2-thienyl)ethyl]-3-methyl-4-(N-phenyl-2-furoylamido)piperidinium oxalate (m.p. 201°–204° C.)

cis-1-[2-(2-thienyl)ethyl]-3-methyl-4-[N-(2-methoxyphenyl)-2-methoxypropionamido]piperidinium oxalate (m.p. 172°–173° C.)

cis-1-(2-phenylethyl)-3-methyl-4-[N-(2-fluorophenyl)-2-furoylamido]piperidinium oxalate (m.p. 178°–179° C.)

cis-1-[2-(4-ethyl-4,5-dihydro-5-oxo-1H-tetrazol-1-yl)ethyl]-3-methyl-4-(N-phenyl-2-furoylamido)piperidinium oxalate (m.p. 124°–125° C.)

Further examples of compounds within the scope of the present invention which could also be prepared by procedures analogous to those described above include:
1-(2-phenylethyl)-4-methoxycarbonyl-4-[N-(2-fluorophenyl)-2-cyclohexyloxypropionamido)piperidine.
1-(n-heptyl)-3-methyl-4-(N-phenyl-2-methoxypropionamido)piperidine.
1-cyclopentylmethyl-4-methoxycarbonyl-4-[N-(2-fluorophenyl)methoxyacetamido]piperidine.
1-(2,2,2-trifluoroethyl)-3-methyl-4-(N-phenylmethoxyaceamido)piperidine.
1-(2-butyn-1-yl)-4-methoxycarbonyl-4-[N-(2-methoxyphenyl)-2-methoxypropionamido]piperidine.
1-(2-propen-1-yl)-4-methoxycarbonyl-4-(N-phenyl-2-methoxypropionamido)piperidine.
1-(2-methyl-2-propen-1-yl)-4-methoxycarbonyl-4-(N-phenylmethoxyacetamido)piperidine.
1-[2-(4-benzyl-4,5-dihydro-5-oxo-1H-tetrazol-1-yl)ethyl]-3-methyl-4-(N-phenylmethoxyacetamido)-piperidine.
1-[2-(4-phenyl-4,5-dihydro-5-oxo-1H-tetrazol-1-yl)ethyl]-4-methoxycarbonyl-4-[N-(2-fluorophenyl)-2-methoxypropionamido]piperidine.
1-[2-(4-cyclopentyl-4,5-dihydro-5-oxo-1H-tetrazol-1-yl)ethyl]-3-methyl-4-(N-phenylmethoxyacetamido)-piperidine.
1-[2-(2-thienyl)ethyl]-4-benzyloxycarbonyl-4-(N-phenylmethoxyacetamido)piperidine.
1-[2-(2-fluorophenyl)ethyl]-4-[(2-phenylpropoxy)carbonyl]-4-(N-phenylmethoxyacetamido)piperidine.
1-(2-phenylethyl)-4[(2-phenoxyethoxy)carbonyl]-4-[N-(2-fluorophenyl)methoxyacetamido]piperidine.
1-[2-(2-thienyl)ethyl]-4-[(2-methoxyethoxy)carbonyl]-4-[N-(2-methoxyphenyl)methoxyacetamido]piperidine.

EXAMPLE XXXII

A pharmaceutical composition for parenteral or intravenous analgesic administration can be prepared from the following ingredients:

| COMPONENTS | AMOUNTS |
| --- | --- |
| 1-[2-(2-thienyl)ethyl]-4-methoxy-carbonyl-4-(N—phenylmethoxyacetamido)-piperidinium citrate | 1 mg. |
| Isotonic water | 10 liters |

Of course, other compounds of the invention can be substituted for 1-[2-(2-thienyl)ethyl]-4-methoxycarbonyl-4-(N-phenylmethoxyacetamido)piperidinium citrate, such as:
1-(2-phenylethyl)-4-[N-(2-fluorophenyl)methoxyacetamido]piperidinium chloride
1-(2-phenylethyl)-4-[N-(2-fluorophenyl)-2-methoxypropionamido]piperidinium chloride
1-(2-phenylethyl)-4-(N-phenylmethoxyacetamido)-piperidinium chloride
1-(2-phenylethyl)-4-(N-phenyl-2-furoylamido)-piperidinium chloride
1-(2-phenylethyl)-4-[(N-phenyl)-2-methoxypropionamido]piperidinium chloride
1-[2-(2-thienyl)ethyl]-4-(N-phenylmethoxyacetamido)-piperidinium citrate
1-(2-phenyl-1-propyl)-4-(N-phenylmethoxyacetamido)-piperidinium citrate
1-(2-phenylethyl)-4-methoxycarbonyl-4-(N-phenylmethoxyacetamido)piperidinium citrate
1-[2-(2-thienyl)ethyl]-4-methoxymethyl-4-(N-phenylmethoxyacetamido)piperidinium citrate
1-(2-phenylethyl)-4-methoxymethyl-4-(N-phenylmethoxyacetamido)piperidinium citrate
1-(2-phenyl-1-propyl)-4-methoxycarbonyl-4-(N-phenylmethoxyacetamido)piperidinium citrate
1-[2-(2-thienyl)ethyl]-3-methyl-4-[N-phenylmethoxyacetamido]piperidinium chloride
trans-1-(2-phenylethyl)-3-methyl-4-[N-(2-fluorophenyl)methoxyacetamido]piperidinium chloride
cis-1-[2-(2-thienyl)ethyl]-3-methyl-4-[N-(2-fluorophenyl)-2-furoylamido]piperidinium chloride
with the relative amount of such other compounds in the composition depending upon their analgesic activity.

EXAMPLE XXXIII

A pharmaceutical composition for parenteral or intravenous analegesic administration can be prepared from the following ingredients:

| COMPONENTS | AMOUNTS |
| --- | --- |
| 1-(2-phenyl-1-propyl)-4-methoxycarbonyl-4-(N—phenylmethoxyacetamido)piperidinium citrate | 10 mg. |
| Isotonic Water | 100 ml |

Again, other compounds of the invention can be substituted for 1-(2-phenyl-1-propyl)-4-methoxycarbonyl-4-(N-phenylmethoxyacetamido)piperidinium citrate with the relative amount of such other compounds in the composition depending upon their analgesic activity.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:
1. A compound of the formula

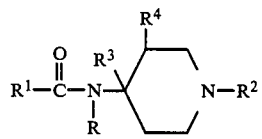

optically active isomeric forms thereof, and/or pharmaceutically acceptable acid addition salts thereof, in which formula: R is selected from the group consisting of phenyl and substituted phenyl wherein the substituents are selected from halogen, cyano, lower-alkoxy, lower-alkyl, lower-alkylenedioxy, halogenated lower-alkyl, lower-alkylthio, or combinations thereof; $R^1$ is a group of the formula

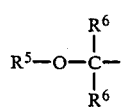

wherein $R^5$ is selected from lower-alkyl, lower-cycloalkyl, halogenated lower-alkyl, phenyl, or phenyl lower-alkyl, and wherein each $R^6$ is independently selected from hydrogen, lower-cycloalkyl or lower-alkyl; R² is selcted from the group consisting of phenyl-lower-alkyl, lower-alkyl, lower-alkenyl, lower-alkynyl, halogenated lower-alkyl, (lower-cycloakyl)-lower-alkyl, (cyclopentyl)-lower-alkyl, thienyl lower-alkyl, thiazolyl lower-alkyl which can be substituted in the 4-position with a methyl group, (4,5-dihydro-5-oxo-1H-tetrazol-1-yl) lower-alkyl which can be substitued in the 4-position with a group selected from lower-alkyl, lower-cycloalkyl, phenyl or phenyl lower-alkyl, and substituted phenyl lower-alkyl in which the substituents on the phenyl ring are selected from halogen, cyano, lower-alkoxy, lower-alkyl, lower-alkylenedioxy, halogenated lower-alkyl, lower-alkylthio or combinations thereof; R³ is selected from a group consisting of hydrogen, methoxymethyl, and a carboxylate radical represented by the formula

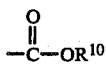

wherein R¹⁰ is selected from the group consisting of lower-alkyl, phenyl-lower-alkyl, lower-alkoxy-lower-alkyl, and phenyloxy-lower-alkyl; and R⁴ is selected from hydrogen or methyl.

2. A compound of the formula

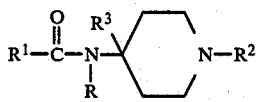

optically active isomeric forms thereof, and/or pharmaceutically acceptable acid addition salts thereof, in which formula: R is selected from the group consisting of phenyl and substituted phenyl wherein the substituents are selected from halogen, lower-alkoxy, lower-alkyl, or combinations thereof; R¹ is a group of the formula

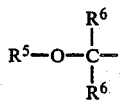

wherein R⁵ is lower-alkyl, or lower-cycloalkyl, and wherein each R⁶ is independently selected from hydrogen, lower-alkyl or lower-cycloalkyl; R² is a group of the formula

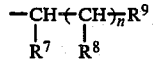

wherein each R⁷ and R⁸ are independently selected from hydrogen, phenyl or lower-alkyl, wherein R⁹ is selected from the group consisting of phenyl, thienyl, 4,5-dihydro-5-oxo-1H-tetrazol-1-yl, 4,5-dihydro-5-oxo-1H-tetrazol-1-yl substituted in the 4-position by a group selected from lower-alkyl, phenyl-lower-alkyl or phenyl, and substituted phenyl in which the substituents are selected from halogen, lower-alkoxy, lower-alkyl, or combinations thereof, and wherein n is an integer of from 0 to 7; R³ is selected from a group consisting of hydrogen, methoxy-methyl, and a carboxylate radical represented by the formula

wherein R¹⁰ is selected from lower-alkyl, phenyl-lower-alkyl or lower-alkoxy-lower-alkyl.

3. A compound of the formula

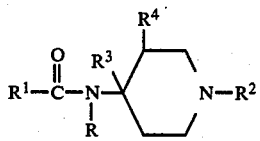

optically active isomeric forms thereof, and/or pharmaceutically acceptable acid addition salts thereof, in which formula: R is phenyl or 2-substituted phenyl wherein said 2-substituent is selected from halogen, lower-alkoxy or lower-alkyl; R¹ is selected from the group consisting of methoxymethyl, 1-methoxyethyl, thienyl and furanyl; R² is selected from the group consisting of benzyl, 2-phenylethyl, 2-(2-fluorophenyl)-ethyl, 1-phenyl-2-propyl, 2-phenyl-1-propyl, 2-(3-thienyl)-ethyl, 2-(2-thienyl)ethyl, 2-(4-methylthiazol-5-yl)ethyl, 2-(4-ethyl-4,5-dihydro-5-oxo-1H-tetrazol-1-yl)ethyl, and 2-methyl-1-propyl; R³ is selected from the group consisting of hydrogen, methoxymethyl and a methyl carboxylate group; and R⁴ is selected from hydrogen or methyl.

4. A compound of the formula

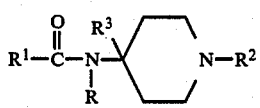

optically active isomeric forms thereof, and/or pharmaceutically acceptable acid addition salts thereof, in which formula: R is phenyl; R¹ is methoxymethyl or furanyl; R² is selected from the group consisting of 2-phenylethyl, 1-phenyl-2-propyl, 2-phenyl-1-propyl, and 2-(2-thienyl)ethyl; and R³ is selected from the group consisting of hydrogen, methoxymethyl and a methyl carboxylate group.

5. A compound according to claim 4, which comprises 1-[2-(2-thienyl)ethyl]-4-methoxycarbonyl-4-(N-phenylmethoxyacetamido)piperidine or a pharmaceutically acceptable acid addition salt thereof.

6. A compound according to claim 4, which comprises 1-[2-(2-thienyl)ethyl]-4-methoxymethyl-4-(N-phenylmethoxyacetamido)piperidine or a pharmaceutically acceptable acid addition salt thereof.

7. A compound according to claim 4, which comprises 1-(2-phenylethyl)-4-methoxycarbonyl-4-(N-phenylmethoxyacetamido)piperidine or a pharmaceutically acceptable acid addition salt thereof.

8. A compound according to claim 4, which comprises 1-(2-phenylethyl)-4-methoxymethyl-4-(N-phenylmethoxyacetamido)piperidine or a pharmaceutically acceptable acid addition salt thereof.

9. A compound according to claim 4, which comprises 1-[2-(2-thienyl)ethyl]-4-(N-phenylmethoxyacetamido)piperidine or a pharmaceutically acceptable acid addition salt thereof.

10. A compound according to claim 4, which comprises 1-(2-phenylethyl)-4-(N-phenyl-2-furoylamido)- piperidine or a pharmaceutically acceptable acid addition salt thereof.

11. A compound according to claim 4, which comprises 1-(2-phenylethyl)-4-(N-phenyl-2-methoxypropionamido)piperidine or a pharmaceutically acceptable acid addition salt thereof.

12. A compound according to claim 4, which comprises 1-(2-phenylethyl)-4-(N-phenylmethoxyacetamido)piperidine or a pharmaceutically acceptable acid addition salt thereof.

13. A compound according to claim 4, which comprises 1-(2-phenyl-1-propyl)-4-methoxycarbonyl-4-(N-phenylmethoxyacetamido)piperidine or a pharmaceutically acceptable acid addition salt thereof.

14. A compound according to claim 3, which comprises 1-(2-phenylethyl)-4-[N-(2-fluorophenyl)methoxyacetamido]piperidine or a pharmaceutically acceptable acid addition salt thereof.

15. A compound according to claim 3, which comprises 1-(2-phenylethyl)-4-[N-(2-fluorophenyl)-2-methoxypropionamido]piperidine or a pharmaceutically acceptable acid addition salt thereof.

16. A compound according to claim 3, which comprises 1-(2-phenylethyl)-4-[N-(2-fluorophenyl)-3-furoylamido]piperidine or a pharmaceutically acceptable acid addition salt thereof.

17. A compound according to claim 3, which comprises 1-(1-phenyl-2-propyl)-4-[N-(2-methoxyphenyl)methoxyacetamido]piperidine or a pharmaceutically acceptable acid addition salt thereof.

18. A compound according to claim 3, which comprises 1-[2-(3-thienyl)ethyl]-4-[N-(2-fluorophenyl)methoxyacetamido]piperidine or a pharmaceutically acceptable acid addition salt thereof.

19. A compound according to claim 3, which comprises 1-[2-(4-methylthiazol-5-yl)ethyl]-4-[N-(2-fluorophenyl)methoxyacetamido]piperidine or a pharmaceutically acceptable acid addition salt thereof.

20. A compound according to claim 3, which comprises 1-[2-(2-fluorophenyl)ethyl]-4-[N-(2-fluorophenyl)methoxyacetamido]piperidine or a pharmaceutically acceptable acid addition salt thereof.

21. A compound according to claim 3, which comprises 1-(1-phenyl-2-propyl)-4-(N-phenyl-methoxyacetamido)piperidine or a pharmaceutically acceptable acid addition salt thereof.

22. A compound according to claim 3, which comprises 1-benzyl-4-methoxycarbonyl-4-(N-phenylmethoxyacetamido)piperidine or a pharmaceutically acceptable acid addition salt thereof.

23. A compound according to claim 3, which comprises 1-(2-methyl-1-propyl)-4-methoxycarbonyl-4-(N-phenylmethoxyacetamido)piperidine or a pharmaceutically acceptable acid addition salt thereof.

24. A compound according to claim 3, which comprises 1-[2-(3-thienyl)ethyl]-4-methoxycarbonyl-4-(N-phenylmethoxyacetamido)piperidine or a pharmaceutically acceptable acid addition salt thereof.

25. A compound according to claim 3, which comprises 1-(3-phenyl-1-propyl)-4-methoxycarbonyl-4-(N-phenylmethoxyacetamido)piperidine or a pharmaceutically acceptable acid addition salt thereof.

26. A compound according to claim 3, which comprises 1-[2-(2-thienyl)ethyl]-3-methyl-4-(N-phenyl-2-methoxypropionamido)piperidine or a pharmaceutically acceptable acid addition salt thereof.

27. A compound according to claim 3, which comprises 1-[2-(2-thienyl)ethyl]-3-methyl-4-(N-phenyl-2-furoylamido)piperidine or a pharmaceutically acceptable acid addition salt thereof.

28. A compound according to claim 3, which comprises 1-[2-(2-thienyl)ethyl]-3-methyl-4-(N-phenylmethoxyacetamido)piperidine or a pharmaceutically acceptable acid addition salt thereof.

29. A compound according to claim 3, which comprises 1-(2-phenylethyl)-3-methyl-4-[N-(2-fluorophenyl)methoxyacetamido]piperidine or a pharmaceutically acceptable acid addition salt thereof.

30. A compound according to claim 3, which comprises 1-[2-(2-thienyl)ethyl]-3-methyl-4-[N-(2-methoxyphenyl)-2-furoylamido]piperidine or a pharmaceutically acceptable acid addition salt thereof.

31. A compound according to claim 3, which comprises 1-[2-(2-thienyl)ethyl]-3-methyl-4-[N-(2-fluorophenyl)methoxyacetamido]piperidine or a pharmaceutically acceptable acid addition salt thereof.

32. A compound according to claim 3, which comprises cis-1-[2-(2-thienyl)ethyl]-3-methyl-4-(N-phenylmethoxyacetamido)piperidine or a pharmaceutically acceptable acid addition salt thereof.

33. A compound according to claim 3, which comprises cis-1-[2-(2-thienyl)ethyl]-3-methyl-4-(N-phenyl-2-methoxypropionamido)piperidine or a pharmaceutically acceptable acid addition salt thereof.

34. A compound according to claim 3, which comprises cis-1-[2-(2-thienyl)ethyl]-3-methyl-4-[N-(2-fluorophenyl)methoxyacetamido]piperidine or a pharmaceutically acceptable acid addition salt thereof.

35. A compound according to claim 3, which comprises trans-1-[2-(2-thienyl)ethyl]-3-methyl-4-[N-(2-fluorophenyl)methoxyacetamido]piperidine or a pharmaceutically acceptable acid addition salt thereof.

36. A compound according to claim 3, which comprises cis-1-[2-(4-ethyl-4,5-dihydro-5-oxo-1H-tetrazol-1-yl)ethyl]-3-methyl-4-[N-(2-fluorophenyl)methoxyacetamido]piperidine or a pharmaceutically acceptable acid addition salt thereof.

37. A compound according to claim 3, which comprises cis-1-[2-(2-thienyl)ethyl]-3-methyl-4-[N-(2-fluorophenyl)-2-methoxypropionamido]piperidine or a pharmaceutically acceptable acid addition salt thereof.

38. A compound according to claim 3, which comprises cis-1-(2-phenylethyl)-3-methyl-4-[N-(2-methoxyphenyl)methoxyacetamido]piperidine or a pharmaceutically acceptable acid addition salt thereof.

39. A compound according to claim 3, which comprises cis-1-[2-(4-ethyl-4,5-dihydro-5-oxo-1H-tetrazol-1-yl)ethyl]-3-methyl-4-[N-(2-fluorophenyl)-2-furoylamido]piperidine or a pharmaceutically acceptable acid addition salt thereof.

40. A compound according to claim 5, which comprises cis-1-(2-phenylethyl)-3-methyl-4-[N-(2-chlorophenyl)methoxyacetamido]piperidine or a pharmaceutically acceptable acid addition salt thereof.

41. A compound according to claim 3, which comprises cis-1-[2-(2-thienyl)ethyl]-3-methyl-4-[N-(2-fluorophenyl)-2-furoylamido]piperidine or a pharmaceutically acceptable acid addition salt thereof.

42. A compound according to claim 3, which comprises cis-1-(2-phenylethyl)-3-methyl-4-[N-(2-fluorophenyl)methoxyacetamido]piperidine or a pharmaceutically acceptable acid addition salt thereof.

43. A compound according to claim 3, which comprises trans-1-(2-phenylethyl)-3-methyl-4-[N-(2-fluorophenyl)methoxyacetamido]piperidine or a pharmaceutically acceptable acid addition salt thereof.

44. A compound according to claim 3, which comprises 1-(2-phenylethyl)-4-[N-(2-methoxyphenyl)-2-methoxyacetamido]piperidine or a pharmaceutically acceptable acid addition salt thereof.

45. An analgesic composition comprising a non-toxic pharmaceutically acceptable carrier and an analgesically effective amount of a compound of the formula

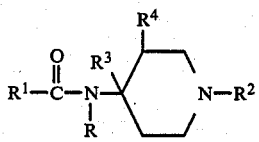

optically active isomeric forms thereof, and/or pharmaceutically acceptable acid addition salts thereof, in which formula: R is selected from the group consisting of phenyl and substituted phenyl wherein the substituents are selected from halogen, cyano, lower-alkoxy, lower-alkyl, lower-alkylenedioxy, halogenated lower-alkyl, lower-alkylthio, or combinations thereof; $R^1$ is a group of the formula

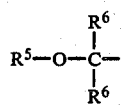

wherein $R^5$ is selected from lower-alkyl, lower-cycloalkyl, halogenated lower-alkyl, phenyl, or phenyl lower-alkyl, and wherein each $R^6$ is independently selected from hydrogen, lower-cycloalkyl or lower-alkyl; $R^2$ is selected from the group consisting of phenyl-lower alkyl, lower-alkyl, lower-alkenyl, lower-alknynyl, halogenated lower-alkyl, (lower-cycloalkyl)-lower-alkyl, (cyclopentyl)-lower-alkyl, thienyl lower-alkyl, thiazolyl lower-alkyl which can be substituted in the 4-position with a methyl group, (4,5-dihydro-5-oxo-1H-tetrazol-1-yl)lower-alkyl which can be substituted in the 4-position with a group selected from lower-alkyl, lower-cycloalkyl, phenyl or phenyl-lower-alkyl, and substituted phenyl lower-alkyl in which the substituents on the phenyl ring are selected from halogen, cyano, lower-alkoxy, lower-alkyl, lower-alkylenedioxy, halogenated lower-alkyl, lower-alkylthio or combinations thereof; $R^3$ is selected from a group consisting of hydrogen, methoxymethyl, and a carboxylate radical represented by the formula

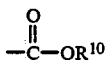

wherein $R^{10}$ is selected from the group consisting of lower-alkyl, phenyl-lower-alkyl, lower-alkoxy-lower-alkyl, and phenyloxy-lower-alkyl; and $R^4$ is selected from hydrogen or methyl.

46. An analgesic composition comprising a non-toxic pharmaceutically acceptable carrier and an analgesically effective amount of a compound of the formula

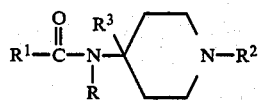

optically active isomeric forms thereof, and/or pharmaceutically acceptable acid addition salts thereof, in which formula: R is selected from the group consisting of phenyl and substituted phenyl wherein the substituents are selected from halogen, lower-alkoxy, lower-alkyl, or combinations thereof; $R^1$ a group of the formula wherein $R^5$ is lower-alkyl, or lower-cycloalkyl, and wherein each $R^6$ is independently selected from hydrogen, lower-alkyl or lower-cycloalkyl; $R^2$ is a group of the formula

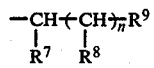

wherein each $R^7$ and $R^8$ are independently selected from hydrogen, phenyl, or lower-alkyl, wherein $R^9$ is selected from the group consisting of phenyl, thienyl, 4,5-dihydro-5-oxo-1H-tetrazol-1-yl, 4,5-dihydro-5-oxo-1H-tetrazol-1-yl substituted in the 4-position by a group selected from lower-alkyl, phenyl-lower-alkyl or phenyl, and substituted phenyl in which the substituents are selected from halogen, lower-alkoxy, lower-alkyl, or combinations thereof, and wherein n is an integer of from 0 to 7; $R^3$ is selected from a group consisting of hydrogen, methoxy-methyl, and a carboxylate radical represented by the formula

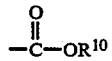

wherein $R^{10}$ is selected from lower-alkyl, phenyl-lower-alkyl or lower-alkoxy-lower-alkyl.

47. An analgesic composition comprising a nontoxic pharmaceutically acceptable carrier and an analgesically effective amount of a compound of the formula

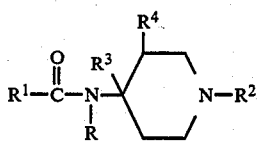

optically active isomeric forms thereof, and/or pharmaceutically acceptable acid addition salts thereof, in which formula: R is phenyl or 2-substituted phenyl wherein said 2-substituent is selected from halogen, lower-alkoxy or lower-alkyl; $R^1$ is selected from the group consisting of methoxymethyl, 1-methoxyethyl, thienyl and furanyl; $R^2$ is selected from the group consisting of benzyl, 2-phenylethyl, 2-(2-fluorophenyl)-ethyl, 1-phenyl-2-propyl, 2-phenyl-1-propyl, 2-(3-thienyl)-ethyl, 2-(2-thienyl)ethyl, 2-(4-methylthiazol-5-yl)ethyl, 2-(4-ethyl-4,5-dihydro-5-oxo-1H-tetrazol-1-yl)ethyl, and 2-methyl-1-propyl; $R^3$ is selected from the group consisting of hydrogen, methoxymethyl and a methyl carboxylate group; and $R^4$ is selected from hydrogen or methyl.

48. An analgesic composition comprising a nontoxic pharmaceutically acceptable carrier and an analgesically effective amount of a compound of the formula

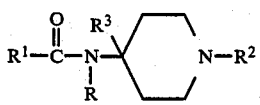

optically active isomeric forms thereof, and/or pharmaceutically acceptable acid addition salts thereof, in which formula: R is phenyl; $R^1$ is methoxymethyl or furanyl; $R^2$ is selected from the group consisting of 2-phenylethyl, 1-phenyl-2-propyl, 2-phenyl-1-propyl, and 2-(2-thienyl)ethyl; and $R^3$ is selected from the group consisting of hydrogen, methoxymethyl and a methyl carboxylate group.

49. An analgesic composition according to claim 48, wherein said compound comprises 1-[2-(2-thienyl)ethyl]-4-methoxycarbonyl-4-(N-phenylmethoxyacetamido)piperidine or a pharmaceutically acceptable acid addition salt thereof.

50. An analgesic composition according to claim 48, wherein said compound comprises 1-[2-(2-thienyl)ethyl]-4-methoxymethyl-4-(N-phenylmethoxyacetamido)piperidine or a pharmaceutically acceptable acid addition salt thereof.

51. An analgesic composition according to claim 48, wherein said compound comprises 1-(2-phenylethyl)-4-methoxycarbonyl-4-(N-phenylmethoxyacetamido)piperidine or a pharmaceutically acceptable acid addition salt thereof.

52. An analgesic composition according to claim 48, wheren said compound comprises 1-(2-phenylethyl)-4-methoxymethyl-4-(N-phenylmethoxyacetamido)piperidine or a pharmaceutically acceptable acid addition salt thereof.

53. An analgesic composition according to claim 48, wherein said compound comprises 1-[2-(2-thienyl)ethyl]-4-(N-phenylmethoxyacetamido)piperidine or a pharmaceutically acceptable acid addition salt thereof.

54. An analgesic composition according to claim 48, wherein said compound comprises 1-(2-phenylethyl)-4-(N-phenyl-2-furoylamido)piperidine or a pharmaceutically acceptable acid addition salt thereof.

55. An analgesic composition according to claim 48, wherein said compound comprises 1-(2-phenylethyl)-4-(N-phenyl-2-methoxypropionamido)piperidine or a pharmaceutically acceptable acid addition salt thereof.

56. An analgesic composition according to claim 48, wherein said compound comprises 1-(2-phenylethyl)-4-(N-phenylmethoxyacetamido)piperidine or a pharmaceutically acceptable acid addition salt thereof.

57. An analgesic composition according to claim 48, wherein said compound comprises 1-(2-phenyl-1-propyl)-4-methoxycarbonyl-4-(N-phenylmethoxyacetamido)piperidine or a pharmaceutically acceptable acid addition salt thereof.

58. An analgesic composition according to claim 47, wherein said compound comprises 1-(2-phenylethyl)-4-[N-(2-fluorophenyl)methoxyacetamido]piperidine or a pharmaceutically acceptable acid addition salt thereof.

59. An analgesic composition according to claim 47, wherein said compound comprises 1-(2-phenylethyl)-4-[N-(2-fluorophenyl)-2-methoxypropionamido]piperidine or a pharmaceutically acceptable acid addition salt thereof.

60. An analgesic composition according to claim 47, wherein said compound comprises 1-(2-phenylethyl)-4-[N-(2-fluorophenyl)-3-furoylamido]piperidine or a pharmaceutically acceptable acid addition salt thereof.

61. An analgesic composition according to claim 47, which comprises 1-(1-phenyl-2-propyl)-4-[N-(2-methoxyphenyl)methoxyacetamido]piperidine or a pharmaceutically acceptable acid addition salt thereof.

62. An analgesic composition according to claim 47, wherein said compound comprises 1-[2-(3-thienyl)ethyl]-4-[N-(2-fluorophenyl)methoxyacetamido]piperidine or a pharmaceutically acceptable acid addition salt thereof.

63. An analgesic composition according to claim 47, wherein said compound comprises 1-[2-(4-methylthiazol-5-yl)ethyl]-4-[N-(2-fluorophenyl)methoxyacetamido]piperidine or a pharmaceutically acceptable acid addition salt thereof.

64. An analgesic composition according to claim 47, wherein said compound comprises 1-[2-(2-fluorophenyl)ethyl]-4-[N-(2-fluorophenyl)methoxyacetamido]piperidine or a pharmaceutically acceptable acid addition salt thereof.

65. An analgesic composition according to claim 47, wherein said compound comprises 1-(1-phenyl-2-propyl)-4-(N-phenylmethoxyacetamido)piperidine or a pharmaceutically acceptable acid addition salt thereof.

66. An analgesic composition according to claim 47, wherein said compound comprises 1-benzyl-4-methoxycarbonyl-4-(N-phenyl-methoxyacetamido)piperidine or a pharmaceutically acceptable acid addition salt thereof.

67. An analgesic composition according to claim 47, wherein said compound comprises 1-(2-methyl-1-propyl)-4-methoxycarbonyl-4-(N-phenylmethoxyacetamido)piperidine or a pharmaceutically acceptable acid addition salt thereof.

68. An analgesic composition according to claim 47, wherein said compound comprises 1-[2-(3-thienyl)ethyl]-4-methoxycarbonyl-4-(N-phenylmethoxyacetamido)piperidine or a pharmaceutically acceptable acid addition salt thereof.

69. An analgesic composition according to claim 47, wherein said compound comprises 1-(3-phenyl-1-propyl)-4-methoxycarbonyl-4-(N-phenylmethoxyacetamido)piperidine or a pharmaceutically acceptable acid addition salt thereof.

70. An analgesic composition according to claim 47, wherein said compound comprises 1-[2-(2-thienyl)ethyl]-3-methyl-4-(N-phenyl-2-methoxypropionamido)piperidine or a pharmaceutically acceptable acid addition salt thereof.

71. An analgesic composition accordiing to claim 47, wherein said compound comprises 1-[2-(2-thienyl)ethyl]-3-methyl-4-(N-phenyl-2-furoylamido)piperidine or a pharmaceutically acceptable acid addition salt thereof.

72. An analgesic composition according to claim 47, wherein said compound comprises 1-[2-(2-thienyl)ethyl]-3-methyl-4-(N-phenylmethoxyacetamido)piperidine or a pharmaceutically acceptable acid addition salt thereof.

73. An analgesic composition according to claim 47, wherein said compound comprises 1-(2-phenylethyl)-3-methyl-4-[N-(2-fluorophenyl)methoxyacetamido]piperidine or a pharmaceutically acceptable acid addition salt thereof.

74. An analgesic composition according to claim 47, wherein said compound comprises 1-[2-(2-thienyl)ethyl]-3-methyl-4-[N-(2-methoxyphenyl)-2-furoylamido]piperidine or a pharmaceutically acceptable acid addition salt thereof.

75. An analgesic composition according to claim 47, wherein said compound comprises 1-[2-(2-thienyl)ethyl]-3-methyl-4-[N-(2-fluorophenyl)methoxyacetamido]piperidine or a pharmaceutically acceptable acid addition salt thereof.

76. An analgesic composition according to claim 47, wherein said compound comprises cis-1-[2-(2-thienyl)ethyl]-3-methyl-4-(N-phenylmethoxyacetamido)piperidine or a pharmaceutically acceptable acid addition salt thereof.

77. An analgesic composition according to claim 47, wherein said compound comprises cis-1-[2-(2-thienyl)ethyl]-3-methyl-4-(N-phenyl-2-methoxypropionamido)-piperidine or a pharmaceutically acceptable acid addition salt thereof.

78. An analgesic composition according to claim 47, wherein said compound comprises cis-1-[2-(2-thienyl)ethyl]-3-methyl-4-[N-(2-fluorophenyl)methoxyacetamido]piperidine or a pharmaceutically acceptable acid addition salt thereof.

79. An analgesic composition according to claim 47, wherein said compound comprises trans-1-[2-(2-thienyl)ethyl]-3-methyl-4-[N-(2-fluorophenyl)methoxyacetamido]piperidine or a pharmaceutically acceptable acid addition salt thereof.

80. An analgesic composition according to claim 47, wherein said compound comprises cis-1-[2-(4-ethyl-4,5-dihydro-5-oxo-1H-tetrazol-1-yl)ethyl]-3-methyl-4-[N-(2-fluorophenyl)methoxyacetamido]piperidine or a pharmaceutically acceptable acid addition salt thereof.

81. An analgesic composition according to claim 47, wherein said compound comprises cis-1-[2-(2-thienyl)ethyl]-3-methyl-4-[N-(2-fluorophenyl)-2-methoxypropionamido]piperidine or a pharmaceutically acceptable acid addition salt thereof.

82. An analgesic composition according to claim 47, wherein said compound comprises cis-1-(2-phenylethyl)-3-methyl-4-[N-(2-methoxyphenyl)methoxyacetamido]piperidine or a pharmaceutically acceptable acid addition salt thereof.

83. An analgesic composition according to claim 47, wherein said compound comprises cis-1-[2-(4-ethyl-4,5-dihydro-5-oxo-1H-tetrazol-1-yl)ethyl]-3-methyl-4-[N-(2-fluorophenyl)-2-furoylamido]piperidine or a pharmaceutically acceptable acid addition salt thereof.

84. An analgesic composition according to claim 47, wherein said compound comprises cis-1-(2-phenylethyl)-3-methyl-4-[N-(2-chlorophenyl)methoxyacetamido]piperidine or a pharmaceutically acceptable acid addition salt thereof.

85. An analgesic composition according to claim 47, wherein said compound comprises cis-1-[2-(2-thienyl)ethyl]-3-methyl-4-[N-(2-fluorophenyl)-2-furoylamido]-piperidine or a pharmaceutically acceptable acid addition salt thereof.

86. An analgesic composition according to claim 47, wherein said compound comprises cis-1-(2-phenylethyl)-3-methyl-4-[N-(2-fluorophenyl)methoxyacetamido]piperidine or a pharmaceutically acceptable acid addition salt thereof.

87. An analgesic composition according to claim 47, wherein said compound comprises trans-1-(2-phenylethyl)-3-methyl-4-[N-(2-fluorophenyl)methoxyacetamido]piperidine or a pharmaceutically acceptable acid addition salt thereof.

88. An analgesic composition according to claim 47, wherein said compound comprises 1-(2-phenylethyl)-4-[N-(2-methoxyphenyl)-2-methoxyacetamido]piperidine or a pharmaceutically acceptable acid addition salt thereof.

89. A method for providing analgesia in a mammal comprising adminstering to such a mammal an analgesically effective amount of a compound of the formula

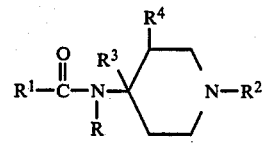

optically active isomeric forms thereof, and/or pharmaceutically acceptable acid addition salts thereof, in which formula: R is selected from the group consisting of phenyl and substituted phenyl wherein the substituents are selected from halogen, cyano, lower-alkoxy, lower-alkyl, lower-alkylenedioxy, halogenated lower-alkyl, lower-alkylthio, or combinations thereof; $R^1$ is a group of the formula

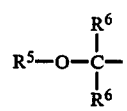

wherein $R^5$ is selected from lower-alkyl, lower-cycloalkyl, halogenated lower-alkyl, phenyl, or phenyl lower-alkyl, and wherein each $R^6$ is independently selected from hydrogen, lower-cycloalkyl or lower-alkyl; $R^2$ is selected from the group consisting of phenyl-lower-alkyl, lower-alkyl, lower-alkenyl, lower-alkynyl, halogenated lower-alkyl, (lower-cycloalkyl)-lower-alkyl, (cyclopentyl)-lower-alkyl, thienyl lower-alkyl, thiazolyl lower-alkyl which can be substitued in the 4-position with a methyl group, (4,5-dihydro-5-oxo-1H-tetrazol-1-yl) lower-alkyl which can be substitued in the 4-position with a group selected from lower-alkyl, lower-cycloalkyl, phenyl or phenyl-lower-alkyl, and substitued phenyl lower-alkyl in which the substituents on the phenyl ring are selected from halogen, cyano, lower-alkoxy, lower-alkyl, lower-alkylenedioxy, halogenated lower-alkyl, lower-alkylthio or combinations thereof; $R^3$ is selected from a group consisting of hydrogen, methoxymethyl, and a carboxylate radical represented by the formula

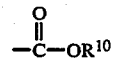

wherein $R^{10}$ is selected from the group consisting of lower-alkyl, phenyl-lower-alkyl, lower-alkoxy-lower-alkyl, and phenyloxyl-lower-alkyl; and $R^4$ is selected from hydrogen or methyl.

90. A method for providing analgesia in a mammal comprising adminstering to such a mammal an analgesically effective amount of a compound of the formula

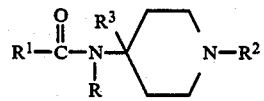

optically active isomeric forms thereof, and/or pharmaceutically acceptable acid addition salts thereof, in which formula: R is selected from the group consisting of phenyl and substituted phenyl wherein the substituents are selected from halogen, cyano, lower-alkoxy, lower-alkyl, lower-alkylenedioxy, halogenated lower-alkyl, lower-alkylthio, or combinations thereof; $R^1$ is a group of the formula

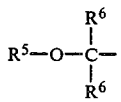

wherein $R^5$ is lower-alkyl, or lower-cycloalkyl, and wherein each $R^6$ is independently selected from hydrogen, lower-alkyl or lower-cycloalkyl; $R^2$ is a group of the formula

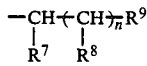

wherein each $R^7$ and $R^8$ are independently selected from hydrogen, phenyl, or lower-alkyl, wherein $R^9$ is selected from the group consisting of phenyl, thienyl, 4,5-dihydro-5-oxo-1H-tetrazol-1-yl, 4,5-dihydro-5-oxo-1H-tetrazol-1-yl substituted in the 4-position by a group selected from lower-alkyl, phenyl-lower-alkyl or phenyl, and substituted phenyl in which the substituents are selected from halogen, lower-alkoxy, lower-alkyl, or combinations thereof, and wherein n is an integer of from 0 to 7; $R^3$ is selected from a group consisting of hydrogen, methoxy-methyl, and a carboxylate radical represented by the formula

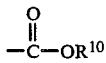

wherein $R^{10}$ is selected from lower-alkyl, phenyl-lower-alkyl or lower-alkoxy-lower-alkyl.

91. A method for providing analgesia in a mammal comprising administering to such a mammal an analgesically effective amount of a compound of the formula

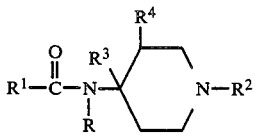

optically active isomeric forms thereof, and/or pharmaceutically acceptable acid addition salts thereof, in which formula: R is phenyl or 2-substituted phenyl wherein said 2-substituent is selected from halogen, lower-alkoxy or lower-alkyl; $R^1$ is selected from the group consisting of methoxymethyl, 1-methoxyethyl, thienyl and furanyl; $R^2$ is selected from the group consisting of benzyl, 2-phenylethyl, 2-(2-fluorophenyl)-ethyl, 1-phenyl-2-propyl, 2-phenyl-1-propyl, 2-(3-thienyl)-ethyl, 2-(2-thienyl)ethyl, 2-(4-methylthiazol-5-yl)ethyl, 2-(4-ethyl-4,5-dihydro-5-oxo-1H-tetrazol-1-yl)ethyl, and 2-methyl-1-propyl; $R^3$ is selected from the group consisting of hydrogen, methoxymethyl and a methyl carboxylate group; and $R^4$ is selected from hydrogen or methyl.

92. A method for providing analgesia in a mammal comprising administering to such a mammal an analgesically effective amount of a compound of the formula

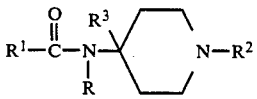

optically active isomeric forms thereof, and/or pharmaceutically acceptable acid addition salts thereof, in which formula: R is phenyl; $R^1$ is methoxymethyl or furanyl; $R^2$ is selected from the group consisting of 2-phenylethyl, 1-phenyl-2-propyl, 2-phenyl-1-propyl, and 2-(2-thienyl)ethyl; and $R^3$ is selected from the group consisting of hydrogen, methoxymethyl and a methyl carboxylate group.

93. A method according to claim 92, wherein said compound comprises 1-[2-(2-thienyl)ethyl]-4-methoxycarbonyl-4-(N-phenylmethoxyacetamido)piperidine or a pharmaceutically acceptable acid addition salt thereof.

94. A method according to claim 92, wherein said compound comprises 1-[2-(2-thienyl)ethyl]-4-methoxymethyl-4-(N-phenylmethoxyacetamido)piperidine or a pharmaceutically acceptable acid addition salt thereof.

95. A method according to claim 92, wherein said compound comprises 1-(2-phenylethyl)-4-methoxycarbonyl-4-(N-phenylmethoxyacetamido)piperidine or a pharmaceutically acceptable acid addition salt thereof.

96. A method according to claim 92, wherein said compound comprises 1-(2-phenylethyl)-4-methoxymethyl-4-(N-phenylmethoxyacetamido)piperidine or a pharmaceutically acceptable acid addition salt thereof.

97. A method according to claim 92, wherein said compound comprises 1-[2-(2-thienyl)ethyl]-4-(N-phenylmethoxyacetamido)piperidine or a pharmaceutically acceptable acid addition salt thereof.

98. A method according to claim 92, wherein said compound comprises 1-(2-phenylethyl)-4-(N-phenyl-2-furoylamido)piperidine or a pharmaceutically acceptable acid addition salt thereof.

99. A method according to claim 92, wherein said compound comprises 1-(2-phenylethyl)-4-(N-phenyl-2-methoxypropionamido)piperidine or a pharmaceutically acceptable acid addition salt thereof.

100. A method according to claim 92, wherein said compound comprises 1-(2-phenylethyl)-4-(N-phenylmethoxyacetamido)piperidine or a pharmaceutically acceptable acid addition salt thereof.

101. A method according to claim 92, wherein said compound comprises 1-(2-phenyl-1-propyl)-4-methoxycarbonyl-4-(N-phenylmethoxyacetamido)piperidine or a pharmaceutically acceptable acid addition salt thereof.

102. A method according to claim 91, wherein said compound comprises 1-(2-phenylethyl)-4-[N-(2-fluorophenyl)methoxyacetamido]piperidine or a pharmaceutically acceptable acid addition salt thereof.

103. A method according to claim 91, wherein said compound comprises 1-(2-phenylethyl)-4-[N-(2-fluorophenyl)-2-methoxypropionamido]piperidine or a pharmaceutically acceptable acid addition salt thereof.

104. A method according to claim 91, wherein said compound comprises 1-(2-phenylethyl)-4-[N-(2-fluorophenyl)-3-furoylamido]piperidine or a pharmaceutically acceptable acid addition salt thereof.

105. A method according to claim 91, wherein said compound comprises 1-(1-phenyl-2-propyl)-4-[N-(2- methoxyphenyl)methoxyacetamido]piperidine or a pharmaceutically acceptable acid addition salt thereof.

106. A method according to claim 91, wherein said compound comprises 1-[2-(3-thienyl)ethyl]-4-[N-(2-fluorophenyl)methoxyacetamido]piperidine or a pharmaceutically acceptable acid addition salt thereof.

107. A method according to claim 91, wherein said compound comprises 1-[2-(4-methylthiazol-5-yl)ethyl]-4-[N-(2-fluorophenyl)methoxyacetamido]piperidine or a pharmaceutically acceptable acid addition salt thereof.

108. A method according to claim 91, wherein said compound comprises 1-[2-(2-fluorophenyl)ethyl]-4-[N-(2-fluorophenyl)methoxyacetamido]piperidine or a pharmaceutically acceptable acid addition salt thereof.

109. A method according to claim 91, wherein said compound comprises 1-(1-phenyl-2-propyl)-4-(N-phenylmethoxyacetamido)piperidine or a pharmaceutically acceptable acid addition salt thereof.

110. A method according to claim 91, wherein said compound comprises 1-benzyl-4-methoxycarbonyl-4-(N-phenylmethoxyacetamido)piperidine or a pharmaceutically acceptable acid addition salt thereof.

111. A method according to claim 91, wherein said compound comprises 1-(2-methyl-1-propyl)-4-methoxycarbonyl-4-(N-phenylmethoxyacetamido)piperidine or a pharmaceutically acceptable acid addition salt thereof.

112. A method according to claim 91, wherein said compound comprises 1-[2-(3-thienyl)ethyl]-4-methoxycarbonyl-4-(N-phenylmethoxyacetamido)piperidine or a pharmaceutically acceptable acid addition salt thereof.

113. A method according to claim 91, wherein said compound comprises 1-(3-phenyl-1-propyl)-4-methoxycarbonyl-4-(N-phenylmethoxyacetamido)piperidine or a pharmaceutically acceptable acid addition salt thereof.

114. A method according to claim 91, wherein said compound comprises 1-[2-(2-thienyl)ethyl]-3-methyl-4-(N-phenyl-2-methoxypropionamido)piperidine or a pharmaceutically acceptable acid addition salt thereof.

115. A method according to claim 91, wherein said compound comprises 1-[2-(2-thienyl)ethyl]-3-methyl-4-(N-phenyl-2-furoylamido)piperidine or a pharmaceutically acceptable acid addition salt thereof.

116. A method according to claim 91, wherein said compound comprises 1-[2-(2-thienyl)ethyl]-3-methyl-4-(N-phenylmethoxyacetamido)piperidine or a pharmaceutically acceptable acid addition salt thereof.

117. A method according to claim 91, wherein said compound comprises 1-(2-phenylethyl)-3-methyl-4-[N-(2-fluorophenyl)methoxyacetamido]piperidine or a pharmaceutically acceptable acid addition salt thereof.

118. A method according to claim 91, wherein said compound comprises 1-[2-(2-thienyl)ethyl]-3-methyl-4-[N-(2-methoxyphenyl)-2-furoylamido]piperidine or a pharmaceutically acceptable acid addition salt thereof.

119. A method according to claim 91, wherein said compound comprises 1-[2-(2-thienyl)ethyl]-3-methyl-4-[N-(2-fluorophenyl)methoxyacetamido]piperidine or a pharmaceutically acceptable acid addition salt thereof.

120. A method according to claim 91, wherein said compound comprises cis-1-[2-(2-thienyl)ethyl]-3-methyl-4-(N-phenylmethoxyacetamido)piperidine or a pharmaceutically acceptable acid addition salt thereof.

121. A method according to claim 91, wherein said compound comprises cis-1-[2-(2-thienyl)ethyl]-3-methyl-4-(N-phenyl-2-methoxypropionamido)piperidine or a pharmaceutically acceptable acid addition salt thereof.

122. A method according to claim 91, wherein said compound comprises cis-1-[2-(2-thienyl)ethyl]-3-methyl-4-[N-(2-fluorophenyl)methoxyacetamido]piperidine or a pharmaceutically acceptable acid addition salt thereof.

123. A method according to claim 91, wherein said compound comprises trans-1-[2-(2-thienyl)ethyl]-3-methyl-4-[N-(2-fluorophenyl)methoxyacetamido]piperidine or a pharmaceutically acceptable acid addition salt thereof.

124. A method according to claim 91, wherein said compound comprises cis-1-[2-(4-ethyl-4,5-dihydro-5-oxo-1H-tetrazol-1-yl)ethyl]-3-methyl-4-[N-(2-fluorophenyl)methoxyacetamido]piperidine or a pharmaceutically acceptable acid addition salt thereof.

125. A method according to claim 91, wherein said compound comprises cis-1-[2-(2-thienyl)ethyl]-3-methyl-4-[N-(2-fluorophenyl)-2-methoxypropionamido]piperidine or a pharmaceutically acceptable acid addition salt thereof.

126. A method according to claim 91, wherein said compound comprises cis-1-(2-phenylethyl)-3-methyl-4-[N-(2-methoxyphenyl)methoxyacetamido]piperidine or a pharmaceutically acceptable acid addition salt thereof.

127. A method according to claim 91, wherein said compound comprises cis-1-[2-(4-ethyl-4,5-dihydro-5-oxo-1H-tetrazol-1-yl)ethyl]-3-methyl-4-[N-(2-fluorophenyl)-2-furoylamido]piperidine or a pharmaceutically acceptable acid addition salt thereof.

128. A method according to claim 91, wherein said compound comprises cis-1-(2-phenylethyl)-3-methyl-4-[N-(2-chlorophenyl)methoxyacetamido]piperidine or a pharmaceutically acceptable acid addition salt thereof.

129. A method according to claim 91, wherein said compound comprises cis-1-[2-(2-thienyl)ethyl]-3-methyl-4-[N-(2-fluorophenyl)-2-furoylamido]piperidine or a pharmaceutically acceptable acid addition salt thereof.

130. A method according to claim 91, wherein said compound comprises cis-1-(2-phenylethyl)-3-methyl-4-[N-(2-fluorophenyl)methoxyacetamido]piperidine or a pharmaceutically acceptable acid addition salt thereof.

131. A method according to claim 91, wherein said compound comprises trans-1-(2-phenylethyl)-3-methyl-4-[N-(2-fluorophenyl)methoxyacetamido]piperidine or a pharmaceutically acceptable acid addition salt thereof.

132. A method according to claim 91, wherein said compound comprises 1-(2-phenylethyl)-4-[N-(2-methoxyphenyl)-2-methoxyacetamido]piperidine or a pharmaceutically acceptable acid addition salt thereof.

* * * * *

UNITED STATES PATENT AND TRADEMARK OFFICE
CERTIFICATE OF CORRECTION

PATENT NO. : 4,584,303

DATED : April 22, 1986

INVENTOR(S) : B. Huang et al

It is certified that error appears in the above-identified patent and that said Letters Patent are hereby corrected as shown below:

Cancel Claims 10, 16, 27, 30, 39, 41, 54, 60, 71, 74, 83, 85, 98, 104, 115, 118, 127 and 129.

In Column 34, Claim 3, lines 21 and 22; Column 38, Claim 47, lines 49 and 50; Column 43, Claim 91, lines 54 and 55, *in each instance*, delete ", 1-methoxyethyl, thienyl and furanyl" and insert in place thereof -- and 1-methoxyethyl -- .

In Column 34, Claim 4, lines 41 and 42; Column 39, Claim 48, lines 3 and 4; and Column 44, Claim 92, lines 9 and 10, *in each instance*, delete "or Furanyl".

Signed and Sealed this

Twenty-first Day of March, 1989

*Attest:*

DONALD J. QUIGG

*Attesting Officer*  *Commissioner of Patents and Trademarks*